US009850529B2

(12) United States Patent
Pierce et al.

(10) Patent No.: US 9,850,529 B2
(45) Date of Patent: Dec. 26, 2017

(54) COMPOSITIONS AND METHODS FOR NUCLEIC ACID BASED DIAGNOSTIC ASSAYS FOR VARIABLE SEQUENCE TARGETS

(75) Inventors: Kenneth E. Pierce, Natick, MA (US); John E. Rice, Quincy, MA (US); Lawrence J. Wangh, Auburndale, MA (US)

(73) Assignee: Brandeis University, Waltham, MA (US)

( * ) Notice: Subject to any disclaimer, the term of this patent is extended or adjusted under 35 U.S.C. 154(b) by 787 days.

(21) Appl. No.: 13/821,287

(22) PCT Filed: Sep. 8, 2011

(86) PCT No.: PCT/US2011/050760
§ 371 (c)(1),
(2), (4) Date: Apr. 23, 2013

(87) PCT Pub. No.: WO2012/033875
PCT Pub. Date: Mar. 15, 2012

(65) Prior Publication Data
US 2013/0203626 A1 Aug. 8, 2013

Related U.S. Application Data

(60) Provisional application No. 61/380,764, filed on Sep. 8, 2010.

(51) Int. Cl.
*C12Q 1/68* (2006.01)
*C12Q 1/70* (2006.01)

(52) U.S. Cl.
CPC ........... *C12Q 1/6858* (2013.01); *C12Q 1/686* (2013.01); *C12Q 1/689* (2013.01); *C12Q 1/6888* (2013.01); *C12Q 1/6895* (2013.01); *C12Q 1/70* (2013.01)

(58) Field of Classification Search
None
See application file for complete search history.

(56) References Cited

U.S. PATENT DOCUMENTS

| | | | |
|---|---|---|---|
| 4,458,066 | A | 7/1984 | Caruthers et al. |
| 5,066,584 | A | 11/1991 | Gyllensten et al. |
| 6,825,010 | B2 | 11/2004 | Spier et al. |
| 7,198,897 | B2 | 4/2007 | Wangh et al. |
| 2004/0053254 | A1* | 3/2004 | Wangh .................. C07H 21/00 435/6.1 |
| 2005/0202436 | A1 | 9/2005 | Gharizadeh |
| 2006/0177841 | A1 | 8/2006 | Wangh et al. |
| 2007/0072211 | A1* | 3/2007 | Newton et al. ................. 435/6 |

FOREIGN PATENT DOCUMENTS

| | | | | |
|---|---|---|---|---|
| KR | WO2009045067 | * | 9/2009 | ............... C12Q 1/68 |
| WO | WO-2008/089519 A1 | | 7/2008 | |
| WO | WO2011019836 | * | 2/2011 | ............... C12Q 1/68 |
| WO | 2011050173 | | 4/2011 | |

OTHER PUBLICATIONS

Bartl S, Weissman IL. PCR primers containing an inosine triplet to complement a variable codon within a conserved protein-coding region. Biotechniques. Feb. 1994; 16(2):246-8, 250.*
Martin FH, Castro MM, Aboul-ela F, Tinoco I Jr. Base pairing involving deoxyinosine: implications for probe design. Nucleic Acids Res. Dec. 20, 1985; 13(24):8927-38.*
Allawi and Santalucia, "Thermodynamics and NMR of Internal G-T Mismatches in DNA," Biochemistry, 1997, 36: 10581-10594.
Ausubel, F. Current Protocols in Molecular Biology (1988) Chapter 15: "The Polymerase Chain Reaction," J. Wiley.
Beaucage et al., "Deoxynucleoside Phosphoramidites—A New Class of Key Intermediates for Deoxypolynucleotide Synthesis," Tetrahedron Letteres, 1981,22: 1859-1862.
Brown et al, "Chemical Synthesis and Cloning of a Tyrosine tRNA Gene," Methods in Enzymology, 1979, 68: 109-151.
Chen et al., "Homologous-restraint polymerase chain reaction: an efficient and rapid protocol to clone multiple homologous genes," Curr. Microbiol., 2008, 57: 51-54.
Duitama et al., "PrimerHunter: a primer design tool for PCR-based virus subtype identification" Nucleic Acids Res., 2009, 37(8): 2483-92.
European Search Report, EP Patent Application No. 11824098.5, mailed Feb. 20, 2014.
Gyllensten and Erlich, "Generation of Single-Stranded DNA by the polymerase chain reaction and its application to direct sequencing of the HLA-DQA Locus," Proc. Natl. Acad. Sci. (USA), 1988, 85: 7652 7656.
International Search Report, International Patent Application No. PCT/US2011/050760, mailed Apr. 10, 2012, 10 pages.
Kwok et al., "A guide to the design and use of mismatched and degenerate primers," Genome Research, 1994, 3(4): S39-S47.
Le Novere, "MELTING, Computing the Melting Temperature of Nucleic Acid Duplex," Bioinformatics, 2001, 17: 1226-7.
Levano-Garcia et al., "Mapping transposon insertion sites by touchdown PCR and hybrid degenerate primers," BioTechniques, 2005, 38(2): 225-229.
Madden et al., "Applications of Network BLAST Server," Meth. Enzymol., 2006, 266: 131 141.
Marras et al., "Multiplex Detection of Single-Nucleotide Variations Using Molecular Beacons," Genet. Anal., 1999, 14:151 156.
Matteucci et al., "Synthesis of Deoxyoligonucleotides on a Polymer Support," J Am Chem Soc, 1981, 103:3185-3191.

(Continued)

*Primary Examiner* — Samuel Woolwine
*Assistant Examiner* — Olayinka Oyeyemi
(74) *Attorney, Agent, or Firm* — Foley Hoag LLP

(57) ABSTRACT

The present invention relates to compositions and methods for nucleic acid based diagnostic assays. In particular, the present invention provides primers for asymmetric PCR and other amplification modalities. In some embodiments, the present invention provides multiple primers for amplification of related nucleic acid targets in a single reaction.

17 Claims, 9 Drawing Sheets

(56) References Cited

OTHER PUBLICATIONS

Matveeva et al., "Identification of regions in multiple sequence alignments thermodynamically suitable for targeting by consensus oligonucleotides: application to HIV genome," BMC Bioinformatics, 2004, 5(1): 44.

Narang et al., "Improved Phosphotriester Method for the Synthesis of Gene Fragments," Meth Enzymol., 1979, 68: 90-99.

Pierce et al., "Design and optimization of a novel reverse transcription linear-after-the-exponential PCR for the detection of foot-and-mouth disease virus," Journal of Applied Microbiology, 2009.

Pierce et al., "Linear-After-The-Exponential (LATE)-PCR: Primer design criteria for high yields of specific single-stranded DNA and improved real-time detection," Proc. Natl. Acad. Sci. (USA), 2005, 102(24):8609-8614.

Poddar, "Symmetric vs. Asymmetric PCR and Molecular Beacon Probe in the Detection of a Target Gene of Adenovirus," Mol. Cell Probes, 2000, 14: 25 32.

Sanchez et al., "Two-temperature LATE-PCR endpoint genotyping," BMC Biotechnology, 2006, 6:44, pp. 1-14.

Sanchez et al., "Linear-After-The-Exponenitial (LATE)-PCR: An advanced method of asymmetirc PCR and its uses in quantitative real-time analysis," Proc. Natl. Acad. Sci. (USA), 2004, 101(7):1933-1938.

Santalucia and Hicks "The Thermodynamics of DNA Structural Motifs", Annu. Rev. Biophys. Biomol. Struct., 2004, 33:415-40.

Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993), Table of Contents Only.

Candrian et al., "Use of Inosine-Containing Oligonucleotide Primers for Enzymatic Amplification of Different Alleles of the Gene Coding for Heat-Stable Toxin Type I of Enterotoxigenic *Escherichia coli*," Appl Environ Microb, 57(4): 955-961 (1991).

European Examination Report for European Application No. 11 824 098.5 dated Sep. 20, 2016.

O'Gorman et al., "Wnt expression is not correlated with β-catenin dysregulation in Dupuytren's Disease," J Negat Results Biomed, 5:13(2006).

\* cited by examiner

FIG. 1
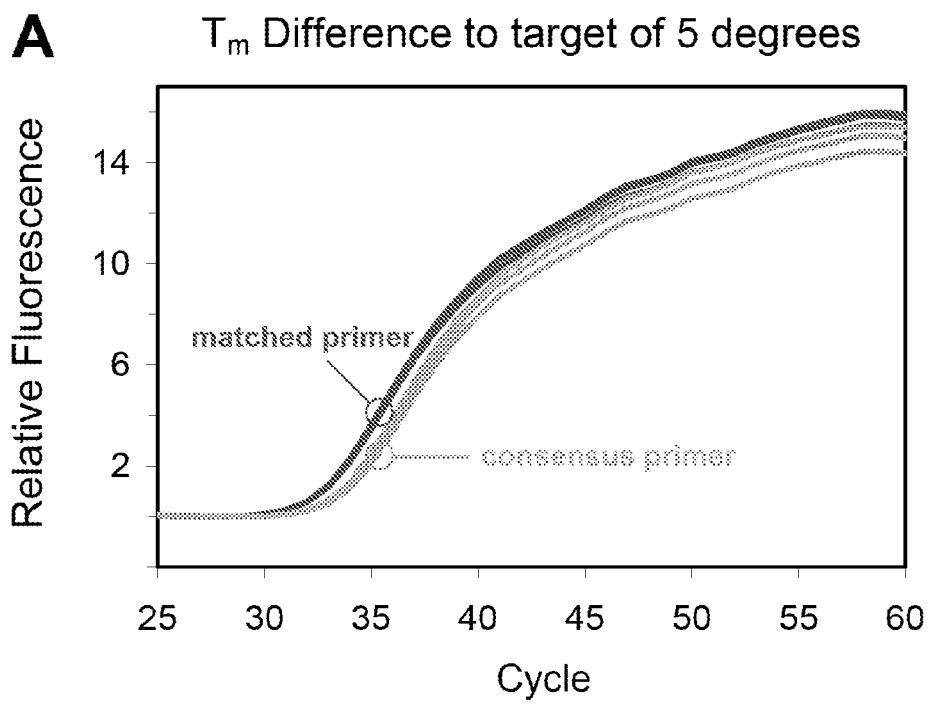
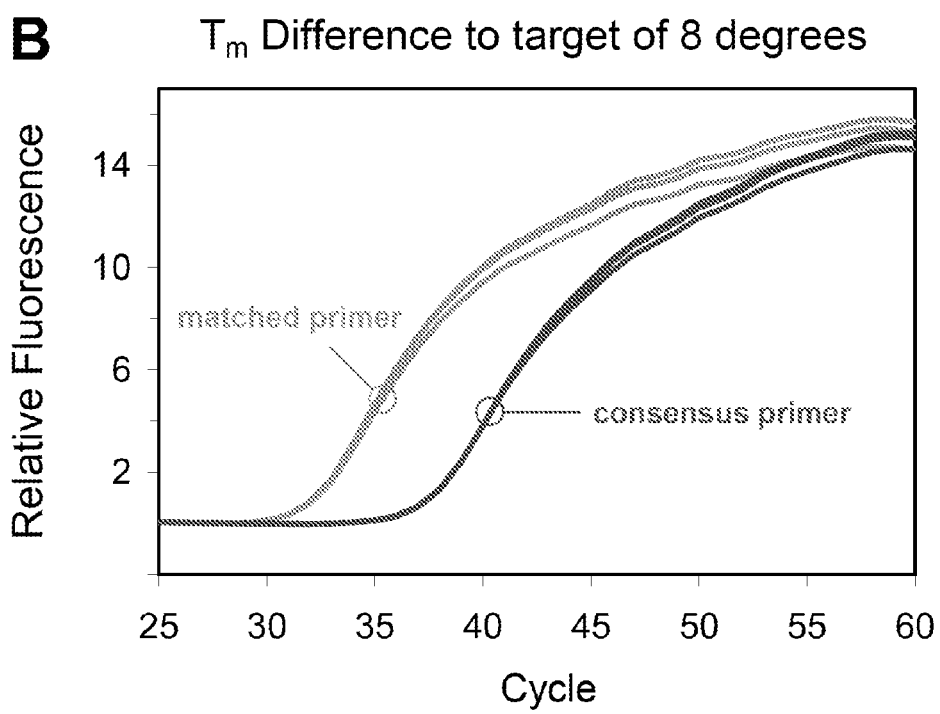

FIG. 1
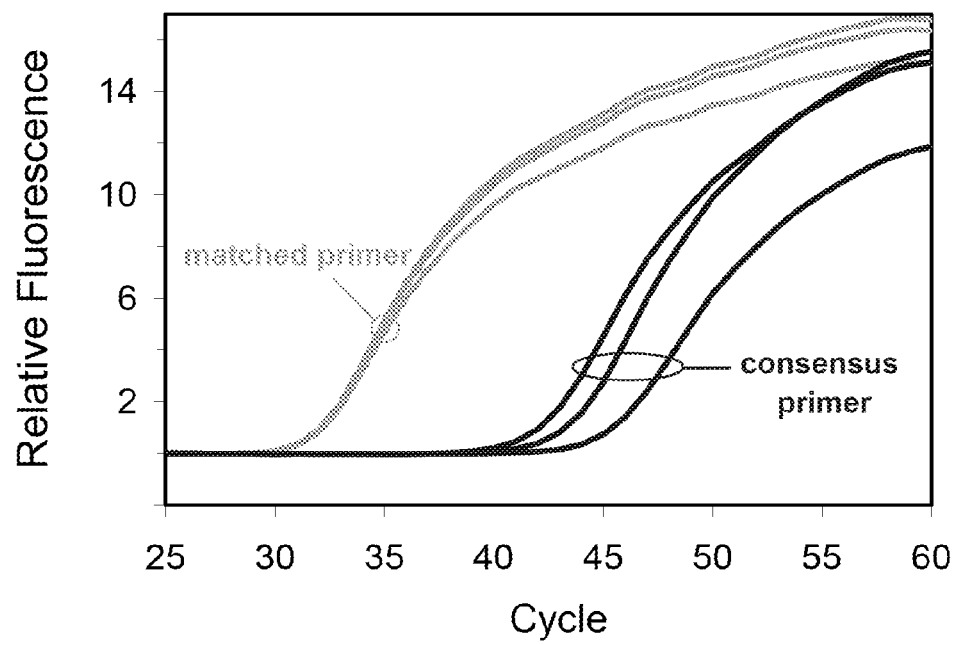
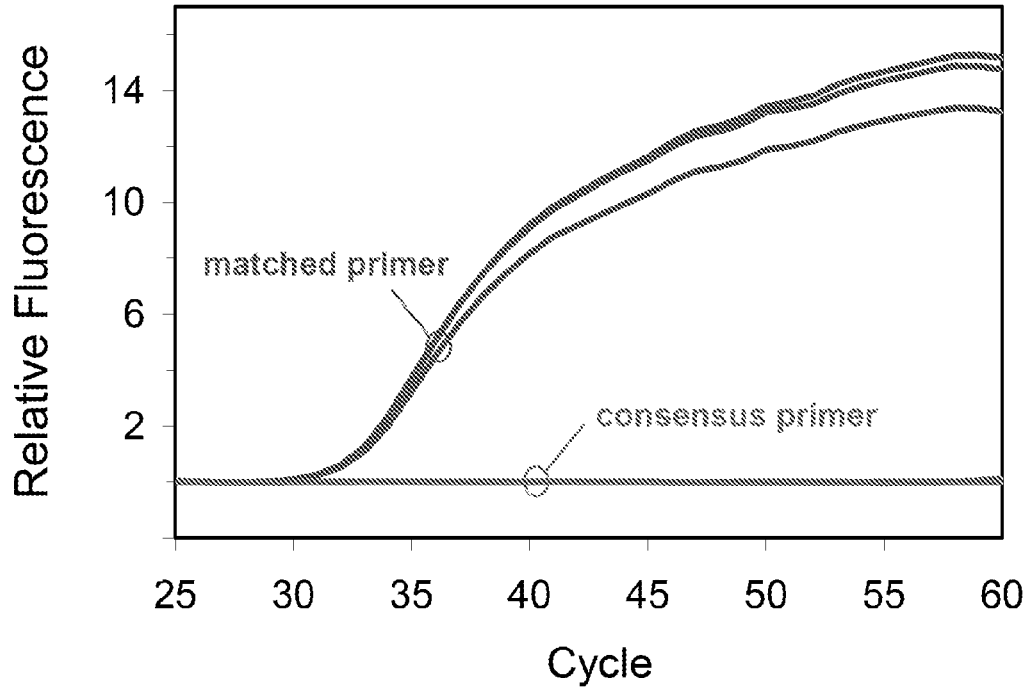

FIG. 3
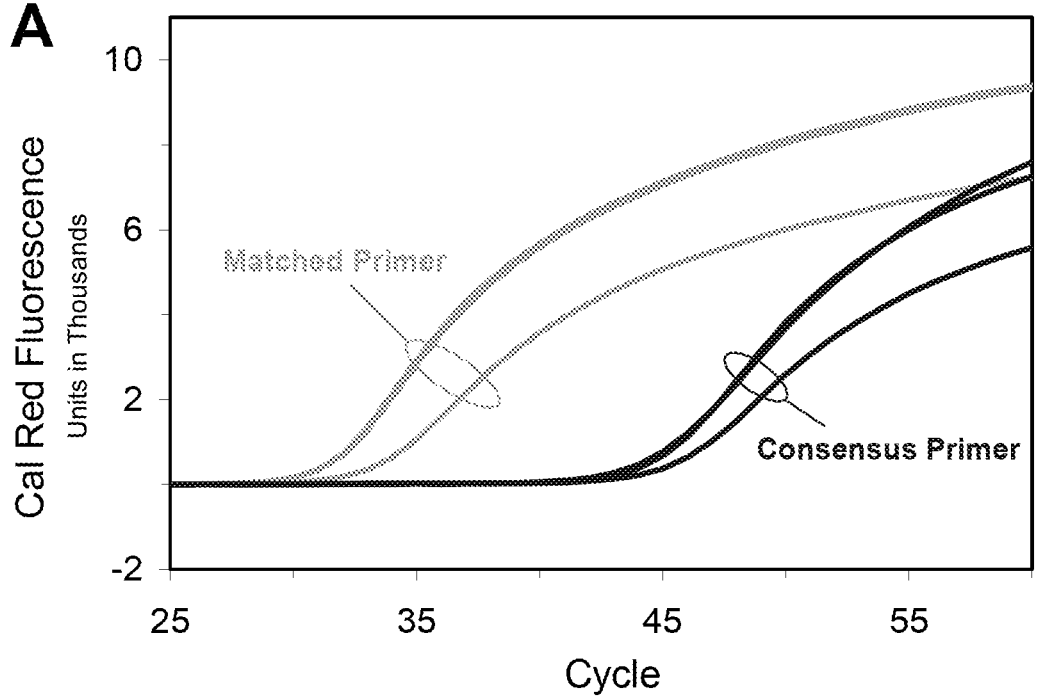
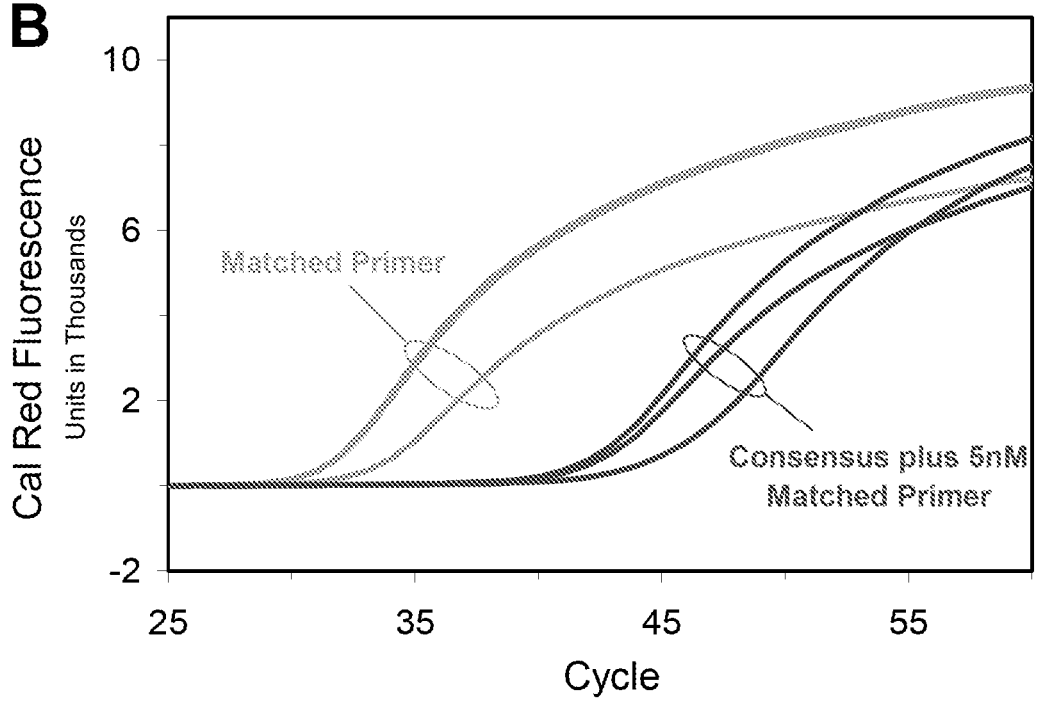

FIG. 3
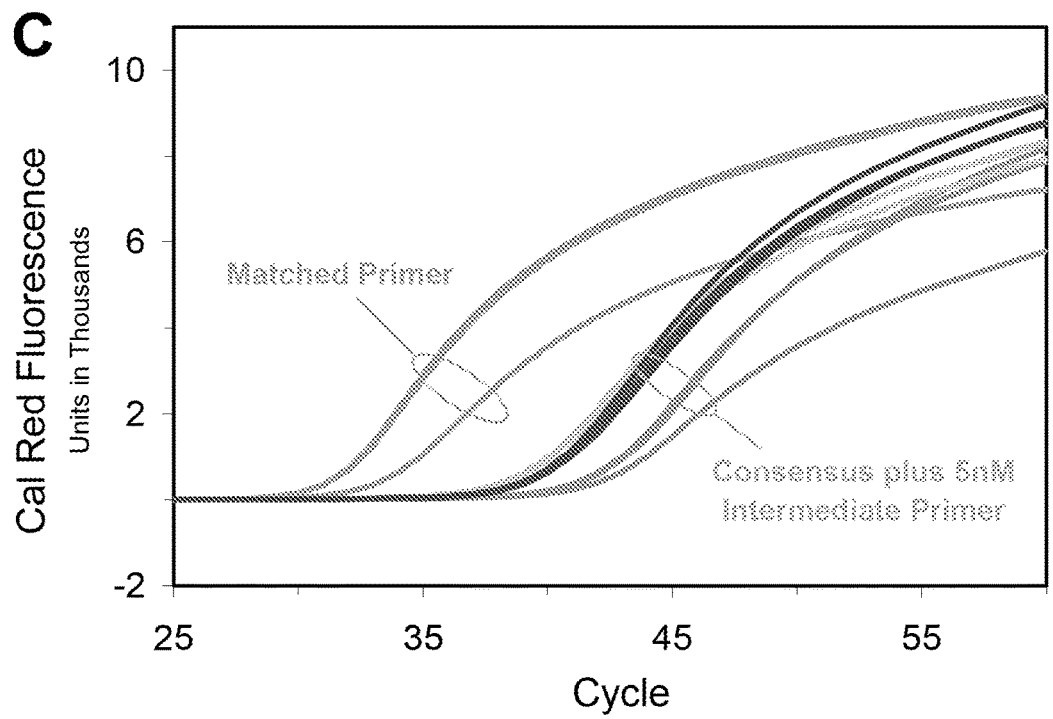
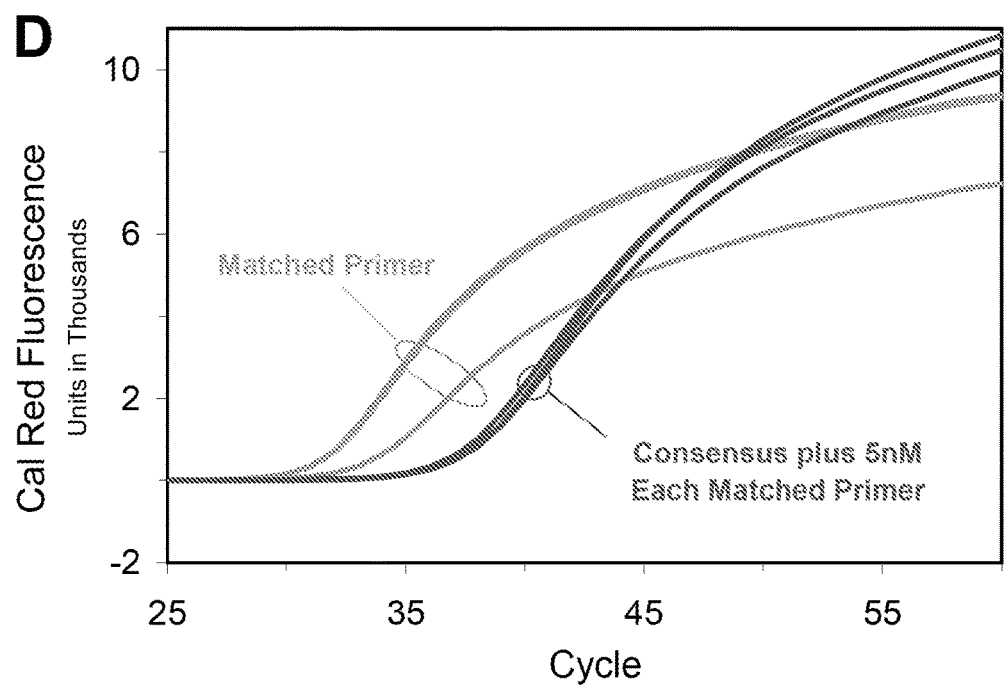

FIG. 4

| primer (isolate name) | -3 | -2 | -1 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | consensus primer Tm[2] | delta Tm[3] | matched primer length | matched primer Tm[4] |
|---|---|---|---|---|---|---|---|---|---|---|---|---|---|---|---|---|---|---|---|---|---|---|---|---|---|---|---|---|---|---|---|---|---|---|---|---|---|---|---|
| consensus primer | | | | A | C | C | A | T | C | A | C | T | G | A | G | C | T | G | T | T | G | A | T | T | C | G | C | A | T | G | A | A | G | C | G | 73.9 | | | |
| 1 IND 23-95 | | | | A | C | C | A | T | C | A | C | T | G | A | G | C | T | G | T | T | G | A | T | T | C | G | C | A | T | G | A | A | A | C | G | 69.9 | 4.0 | 32 nt | 74 |
| 2 IND 339-96 | | | | A | C | C | A | T | C | A | C | T | G | A | G | C | T | G | T | T | G | A | T | T | C | G | C | A | T | G | A | A | A | C | G | 69.0 | 4.9 | 32 nt | 73.7 |
| 3 3kimron iso61 | | | | A | C | C | A | T | C | A | C | T | G | A | G | C | T | G | T | T | G | A | T | T | C | G | C | A | T | G | A | A | A | C | G | 68.8 | 5.1 | 27 | 73.6 |
| 4 IND 82-96 | | | | A | C | C | A | T | C | A | C | T | G | A | G | C | T | G | T | T | G | A | T | T | C | G | C | A | T | G | A | A | A | C | G | 67.5 | 6.4 | 35 nt | 74.4 |
| 5 IND 258-97 | | | | A | C | C | A | T | C | A | C | T | G | A | G | C | T | G | T | T | G | A | T | T | C | G | C | A | T | G | A | A | A | C | G | 66.0 | 7.9 | 34 nt | 73.4 |
| 6 IND 116-90 | | | | A | C | C | A | T | C | A | C | T | G | A | G | C | T | G | T | T | G | A | T | T | C | G | C | A | T | G | A | A | A | C | G | 65.6 | 8.3 | 32 nt | 73.9 |
| 7 TNN 14-93 | | | | A | C | C | A | T | C | T | C | T | G | A | G | C | T | T | T | T | G | A | T | T | C | G | C | A | T | G | A | A | A | C | G | 61.7 | 12.2 | 32 nt | 73.4 |
| 8 IND 324-98 | G | A | C | A | C | C | A | T | C | A | C | T | G | A | G | C | T | G | T | T | G | A | T | T | C | G | C | A | T | G | A | A | A | C | G | 60.3 | 13.6 | 35 nt | 74.4 |
| 9 BR/Myanmar 001-2006 | | | | A | C | C | A | T | C | A | C | T | G | A | G | T | T | G | T | T | G | A | T | T | C | G | C | A | T | C | A | A | A | C | G | 50.4 | 23.5 | 32 nt | 74 |

[1]Nucleotide sequence of the limiting primers, based on known FMDV strain variations. Primer 3 (3kimron iso61) included only nucleotides 6 through 32, although the complements of nucleotides 1 to 5 (boxed) are included in the target and are available to hybridize with the consensus primer. Target specific to primer 4 includes nucleotides complementary to positions -1 to -3. Target specific to primer 8 includes complementary nucleotides at position -3 and -1 and a T at position -2. Positions of the target that mismatch (or extend past) the consensus primer are shaded.

[2]Predicted melting temperature of the consensus primer to each of the target sequences.

[3]Difference between the Tm of the consensus primer to its fully complementary target and the Tm of the consensus primer to the mismatched target.

[4]Predicted Tm of each specific primer to its complemenary target.

FIG. 5

| | Strain / primer | | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | target 324 to specific LP[1] Tm | complement to cons. LP[2] Tm | delta Tm |
|---|---|---|---|---|---|---|---|---|---|---|---|---|---|---|---|---|---|---|---|---|---|---|---|---|---|---|---|---|---|---|---|---|---|---|---|---|---|---|
| SEQ ID NO: 4 | consensus primer | | | A | C | C | A | T | C | A | C | T | G | A | G | C | T | G | T | T | G | A | T | T | C | G | C | A | T | G | A | A | G | C | G | | 73.9 | |
| SEQ ID NO: 12 | IND 324-98 | G | G | C | A | C | A | C | T | G | A | G | C | T | T | T | G | A | T | C | G | C | A | T | G | A | A | C | G | | | | | | | 70.6 | 60.3 | 13.6 |
| SEQ ID NO: 6 | IND 339-96 | | | A | C | C | A | T | C | A | C | T | G | A | G | C | T | G | T | T | G | A | T | C | G | C | A | T | G | A | A | A | C | G | G | 64.9 | 69.0 | 4.9 |
| SEQ ID NO: 10 | IND 116-90 | G | G | A | C | C | A | T | C | A | C | T | G | A | G | C | T | T | T | T | G | A | T | T | C | G | C | A | T | G | A | A | A | C | G | 66.2 | 65.6 | 8.3 |
| SEQ ID NO: 5 | IND 23-95 | | | A | C | C | A | T | C | A | C | T | G | A | G | C | T | T | T | T | G | A | T | C | G | C | A | T | G | A | A | G | C | G | G | 64.7 | 69.9 | 4.0 |

[1] specific limiting primer at 5 nM
[2] consensus limiting primer at 50 nM

COMPOSITIONS AND METHODS FOR NUCLEIC ACID BASED DIAGNOSTIC ASSAYS FOR VARIABLE SEQUENCE TARGETS

CROSS-REFERENCE TO RELATED APPLICATIONS

The present application is a §371 National Entry of PCT/US2011/050760, filed Sep. 8, 2011, which claims the benefit of U.S. Provisional Patent Application 61/380,764, filed Sep. 8, 2010, each of which are incorporated by reference in their entireties.

FIELD OF THE INVENTION

The present invention relates to compositions and methods for nucleic acid based diagnostic assays. In particular, the present invention provides primers for symmetric PCR, asymmetric PCR and other amplification modalities. In some embodiments, the present invention provides multiple primers for amplification of related nucleic acid targets in a single reaction.

BACKGROUND

As the volume of genetic sequence information available increases, genomics research and subsequent drug design efforts increase as well. A number of institutions are actively mining the available genetic sequence information to identify correlations between genes, gene expression and phenotypes (e.g., presence and/or identity of pathogens in sample, disease states, metabolic responses, and the like).

Despite substantial efforts made, existing approaches for analyzing nucleic acid molecules still suffer from inaccuracies and/or inefficiencies and may not provide sufficient information that is accurate, fast, and cost effective.

Thus, the art is in need of improved methodologies.

SUMMARY OF THE INVENTION

The present invention relates to compositions and methods for nucleic acid based diagnostic assays. In particular, the present invention provides primers for symmetric PCR, asymmetric PCR and other amplification modalities. In some embodiments, the present invention provides multiple primers for amplification of related nucleic acid targets in a single reaction.

Embodiments of the present invention provide a method for identifying the presence of any (e.g., one or more, two or more, etc.) of a plurality of related target sequences in a sample, comprising: contacting a sample comprising a target sequence that is one of a plurality of related target sequences, wherein the target sequences differ by at least one nucleotide, with a pair of primers for amplifying one or more of the targets, wherein at least one of the primers contacts positions of the targets or their complements that differ by at least one nucleotide in those positions; and performing an amplification reaction under conditions such that the target sequence is amplified (e.g., in a single reaction); and detecting an amplification product. In some embodiments, the at least one primer is a thermodynamic consensus primer. In some embodiments, the plurality of related targets vary at 4 or more nucleotide position in the region contacted by the thermodynamic consensuses primer. In some embodiments, the method is symmetric PCR. In some embodiments (e.g., asymmetric PCR embodiments), the concentration of the primers is at a ratio of at least 5 to 1. In some embodiments, the single primer that hybridizes to the plurality of related target sequences is at a higher concentration than the two or more primer sequences that hybridize to different members of the plurality of related target sequences. In some embodiments, both the first primers and the second primers comprise multiple primers. In some embodiments, the amplification reaction is polymerase chain reaction (PCR) (e.g., symmetric PCR or asymmetric PCR such as LATE-PCR). In some embodiments, the second primer comprises a limiting primer and the first primer comprises an excess primer, wherein the excess primer is added to the combined sample at a concentration at least five-times that of the limiting primer. In some embodiments, the initial melting temperature of the limiting primer with respect to the target nucleic is higher than or equal to the initial melting temperature of the excess primer with respect to the target nucleic acid. In some embodiments, the plurality of related targets are variants of genes, homologs of genes, orthologs of genes, or subtypes of genes. Exemplary genes include, but are not limited to genes from pathogenic agents (e.g., viruses, bacteria, or fungi), animals (e.g., humans, livestock, or companion animals), or other organisms of interest.

In some embodiments, the present invention provides a method for identifying the presence of any of a plurality of related target sequences in a sample, comprising: A) Contacting a sample comprising a target sequence that is one of a plurality of related target sequences, wherein the target sequences differ by at least one nucleotide, with a pair of primers for amplifying one or more of the targets, wherein at least one of the primers is complementary to a region of the targets or their complements that differ by at least one nucleotide, and wherein at least of the primers is a plurality of primers that are complementary or partially complementary to regions of the targets, and wherein at least one of the plurality of primers is used at a concentration at least 5 times that of other primers in the plurality of primers; B) performing an amplification reaction under conditions such that the target sequence is amplified in a single reaction; and C) detecting an amplification product.

Further embodiments of the present invention provide systems for carrying out any one or more of the steps of the methods described herein. In some embodiments, the systems comprise a processor and/or software configured to generate melting curves of nucleic acids generated from an amplification reactions described herein. In some embodiments, the melting curves identify the target sequence. In some embodiments, the system comprises a display screen wherein results (melting curves, target identity, or other data or analysis) are displayed on the display screen. In some embodiments, the system further comprises instruments for isolating and/or amplifying nucleic acid molecules.

Additional embodiments of the present invention provide kits or systems comprising one or more of a) reagents for performing an amplification reaction for identifying the presence of any of a plurality of related target sequences in a sample, wherein the reagents comprise a) a first primer that is partially or completely complementary to all of the plurality of target sequences; and b) a plurality of second primers, wherein the second primers are present in limiting quantities, and wherein the plurality of second primers hybridizes to each of the related targets at the position wherein the target sequences differ by at least one nucleotide; and c) a processor or software program configured to generate melting curves from an amplification reaction performed using the reagents. In some embodiments, the reagents further comprise reagents for isolation of nucleic acids from the sample and reagents for analyzing amplification products. In some embodiments, reagents are provided in a reagent housing that comprises all of the components necessary, sufficient, or useful for identifying the target sequences.

For example, in some embodiments, the present invention provides an oligonucleotide set comprising a first primer and at least one second primer, wherein the at least one second primer is between 50% and 98% homologous to the first primer, and wherein the concentration of the first primer is at least 5 times higher than the concentration of the second primer. Further embodiments provide an oligonucleotide set comprising a first primer, and at least one second primer, and at least one third primer, wherein the second primer is between 50% and 98% homologous to the first primer, and wherein the concentration of the first primer is at least 5 times higher than the concentration of the second primer, and wherein the third primer is paired with the first primer for the amplification of any of a plurality of related target sequences. In some embodiments, the third primer is at a concentration at least 5 times higher than the concentration of the first primer.

Additional embodiments are described herein.

DESCRIPTION OF THE FIGURES

FIGS. 1A-1D show LATE-PCR amplification of synthetic DNA targets with different sequences at the location to which the limiting primer hybridizes.

FIGS. 3A-3D show LATE-PCR amplification of the synthetic target of FIG. 1C using different sequence-related limiting primers individually and in combination.

FIG. 4 shows the sequences of consensus and specific limiting primers for FMDV 1D gene (SEQ ID NO: 4-SEQ ID NO: 13).

Figure 2:
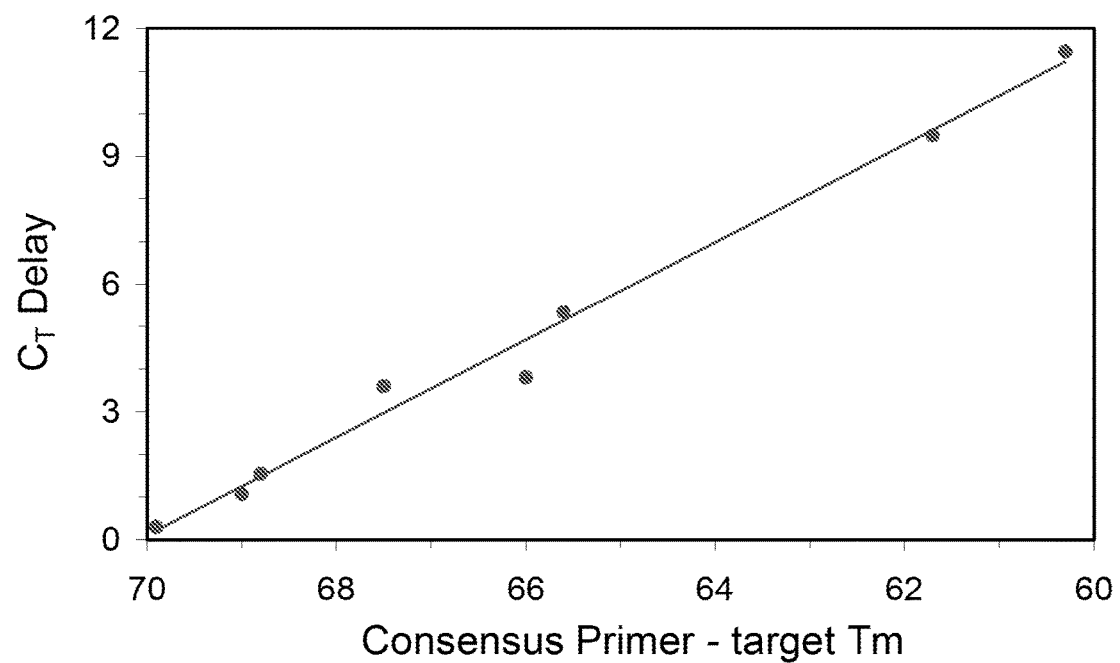
FIG. 2 shows a linear relationship between the $T_M$ of the consensus limiting primer with each of 8 targets and the increase in mean Ct value compared to that obtained with a specific limiting primer for a given target.

FIG. 5 shows sequences and melting temperatures of limiting primers used in Example 2.

FIG. 6 shows the results of amplification of the M1 (6A) and M2 (6B) targets (estimated 10,000 plasmid targets/sample) in Example 4 with different excess primers. FIG. 6 shows the increase in fluorescence of SYBR Green, a double-stranded DNA binding dye during real-time detection.

FIG. 7 shows the post-PCR hybridization results from Example 5, including where multiple limiting and excess primers were used (FIG. 7A), wherein consensus limiting and excess primers were used (FIG. 7B), and wherein consensus plus intermediate primers were used (FIG. 7C).

DEFINITIONS

As used herein, the phrase "hybridization sequence" is used in reference to a particular target sequence and a particular probe or primer, and it is the sequence in the target sequence that hybridizes to the particular probe or primer. The probe or primer may be fully or partially complementary to the target sequence over the length of the hybridization sequence.

As used herein, the term "amplicon" refers to a nucleic acid generated using primer pairs in an amplification reaction (e.g., PCR), such as those described herein. The amplicon is typically single-stranded DNA (e.g., the result of asymmetric amplification), however, it may be RNA or dsDNA.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. In certain embodiments, the type of amplification is asymmetric PCR (e.g., LATE-PCR) which is described in, for example, U.S. Pat. No. 7,198,897 and Sanchez et al., Proc. Natl. Acad. Sci. (USA), 101(7):1933-1938 and Pierce et al., Proc. Natl. Acad. Sci. (USA), 2005, 102(24):8609-8614, all of which are herein incorporated by reference in their entireties. In particular embodiments, LATE-PCR is employed using multiple end-point temperature detection (see, e.g., U.S. Pat. Pub. 2006/0177841 and Sanchez et al., BMC Biotechnology, 2006, 6:44, pages 1-14, both of which are herein incorporated by reference).

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology," "homologous" and "sequence identity" refer to a degree of identity. There may be partial homology or complete homology. A partially homologous sequence is one that is less than 100% identical to another sequence. Determination of sequence identity is described in the following example: a primer 20 nucleobases in length which is otherwise identical to another 20 nucleobase primer but having two non-identical residues has 18 of 20 identical residues (18/20=0.9 or 90% sequence identity). In another example, a primer 15 nucleobases in length having all residues identical to a 15 nucleobase segment of a primer 20 nucleobases in length would have 15/20=0.75 or 75% sequence identity with the 20 nucleobase primer. Sequence identity may also encompass alternate or "modified" nucleobases that perform in a functionally similar manner to the regular nucleobases adenine, thymine, guanine and cytosine with respect to hybridization and primer extension in amplification reactions. In a non-limiting example, if the 5-propynyl pyrimidines propyne C and/or propyne T replace one or more C or T residues in one primer which is otherwise identical to another primer in sequence and length, the two primers will have 100% sequence identity with each other. In another non-limiting example, Inosine (I) may be used as a replacement for G or T and effectively hybridize to C, A or U (uracil). Thus, if inosine replaces one or more G or T residues in one primer which is otherwise identical to another primer in sequence and length, the two primers are considered to have 100% sequence identity with each other, in order to distinguish this type of hybridization from a destabilizing mismatch. Other such modified or universal bases may exist which would perform in a functionally similar manner for hybridization and amplification reactions and will be understood to fall within this definition of sequence identity.

As used herein, the term "hybridization" or "hybridize" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, the melting temperature ($T_M$) of the formed hybrid, and the percentage of residues that are G or C (% GC) within the nucleic acids. A single molecule that contains pairing of complementary nucleic acids within its structure is said to be "self-hybridized." An extensive guide to nucleic hybridization may be found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993), which is incorporated by reference.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method. In certain embodiments, the primer is a capture primer.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N-6-methyladenosine, aziridinylcytosine, pseudoisocytosine, 5-(carboxyhydroxyl-methyl)uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP). As is used herein, a nucleobase includes natural and modified residues, as described herein.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., H', $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth Enzymol.* 68: 90-99; the phosphodiester method of Brown et al. (1979) *Meth Enzymol.* 68: 109-151; the diethylphosphoramidite method of Beaucage et al. (1981) *Tetrahedron Lett.* 22: 1859-1862; the triester method of Matteucci et al. (1981) *J Am Chem. Soc.* 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

As used herein a "sample" refers to anything capable of being analyzed by the methods provided herein. In some embodiments, the sample comprises or is suspected to comprise one or more nucleic acids capable of analysis by the methods. In some embodiments, the samples comprise nucleic acids (e.g., DNA, RNA, cDNAs, etc.) from one or more pathogens or bioagents. Samples can include, for example, blood, saliva, urine, feces, anorectal swabs, vaginal swabs, cervical swabs, and the like. In some embodiments, the samples are "mixture" samples, which comprise nucleic acids from more than one subject or individual. In some embodiments, the methods provided herein comprise purifying the sample or purifying the nucleic acid(s) from the sample. In some embodiments, the sample is purified nucleic acid. In some embodiments, the sample comprises two or more strains or subtypes of the same microorganism.

"$T_M$," or "melting temperature," of an oligonucleotide describes the temperature (in degrees Celsius) at which 50% of the molecules in a population of a single-stranded oligonucleotide are hybridized to their complementary sequence and 50% of the molecules in the population are not-hybridized to said complementary sequence. The $T_M$ of a primer or probe can be determined empirically by means of a melting curve. In some cases it can also be calculated. For the design of symmetric PCR primer pairs, balanced $T_M$'s are generally calculated by one of the three methods discussed earlier, that is, the "% GC", or the "2(A+T) plus 4(G+C)", or "Nearest Neighbor" formula at some chosen set of conditions of monovalent salt concentration and primer concentration. The use of Nearest Neighbor calculations the $T_M$'s of both primers is more accurate, and is particularly important in the case of asymmetric PCR, as $T_M$'s depend on the concentrations chosen for use in calculation or measurement. The following equation is an example of a Nearest Neighbor formula, $T_M = \Delta H/(\Delta S + R \ln(C/2)) - 273.15 + 12 \log [M]$. This formula is based on the published formula (Le Novere, N. (2001), "MELTING, Computing the Melting Temperature of Nucleic Acid Duplex," Bioinformatics 17: 1226 7). $\Delta H$ is the enthalpy and $\Delta S$ is the entropy (both $\Delta H$ and $\Delta S$ calculations are based on Allawi and SantaLucia, 1997), C is the concentration of the oligonucleotide (e.g., $10^{-6}$M), R is the universal gas constant, and [M] is the molar concentration of monovalent cations (e.g., 0.05). According to this formula the nucleotide base composition of the oligonucleotide (contained in the terms $\Delta H$ and $\Delta S$), the monovalent salt concentration, and the concentration of the oligonucleotide (contained in the term C) influence the $T_M$. In general for oligonucleotides of the same length, the $T_M$ increases as the percentage of guanine and cytosine bases of the oligonucleotide increases, but the $T_M$ decreases as the concentration of the oligonucleotide decreases. The concentration of divalent cations such as magnesium, which are present in most amplification reactions, have a strong effect on $T_M$, but are typically not included in most of the commonly used formulas, including the nearest neighbor equation above. Even so, the equation is useful for estimating relative $T_M$'s of different primers. In some embodiments, $T_M$ is obtained using Visual OMP computer software (DNA Software), which utilizes a Nearest Neighbor formula plus proprietary factors for estimating the effects of magnesium and particular nucleotide mismatches. In the case of a primer with nucleotides other than A, T, C and G or with covalent modification, $T_M$ is measured empirically by hybridization melting analysis as known in the art.

"$T_M[0]$" means the $T_M$ of a PCR primer or probe at the start of a PCR amplification taking into account its starting concentration, length, and composition. Unless otherwise stated, $T_M[0]$ is the calculated $T_M$ of a PCR primer at the actual starting concentration of that primer in the reaction mixture, under assumed conditions of 0.05 M monovalent cations and the presence of far lower concentration (e.g., 100 fold) of a target oligonucleotide having a sequence complementary to that of the primer. In instances where a target sequence is not fully complementary to a primer it is important to consider not only the $T_M[0]$ of the primer against its complements but also the concentration-adjusted melting point of the imperfect hybrid formed between the primer and the target. In some embodiments, $T_M[0]$ for a primer is calculated using Visual OMP software as stated in the previous paragraph, using the actual starting concentration of the primer. In the case of a primer with nucleotides other than A, T, C and G that cannot be estimated using Visual OMP, or with covalent modification, $T_M[0]$ is measured empirically by hybridization melting analysis as known in the art.

As used herein superscript X refers to the Excess Primer, superscript L refers to the Limiting Primer, superscript A refers to the amplicon, and superscript P refers to the probe.

$T_M^A$ means the melting temperature of an amplicon, either a double-stranded amplicon or a single-stranded amplicon hybridized to its complement. The melting point of an amplicon, or $T_M^A$ can be calculated by the following % GC formula: $T_M^A = 81.5 + 0.41(\% G + \% C) - 500/L + 16.6 \log [M]/(1+0.7 [M])$, where L is the length in nucleotides and [M] is the molar concentration of monovalent cations. In some embodiments, $T_M^A$ is calculated using Visual OMP, which utilizes a factor for magnesium concentration not included in the % GC formula. $T_M^A$ can also be determined empirically following amplification using a double-stranded DNA-binding dye such as SYBR Green in combination with melting analysis as is well known by those skilled in the art.

$T_M^P$ refers to the concentration-adjusted melting temperature of the probe to its target, or the portion of probe that actually is complementary to the target sequence (e.g., the loop sequence of a molecular beacon probe). In the case of most linear probes, $T_M^P$ is calculated using the Nearest Neighbor formula given above or using Visual OMP, as for primer $T_M$, or preferably is measured empirically. In the case of molecular beacons, a rough estimate of $T_M^P$ can be calculated using commercially available computer programs that utilize the % GC method, see Marras, S. A. et al. (1999) "Multiplex Detection of Single-Nucleotide Variations Using Molecular Beacons," Genet. Anal. 14:151 156, or using the Nearest Neighbor formula, or preferably is measured empirically. In the case of probes having non-conventional bases and for double-stranded probes, $T_M^P$ is determined empirically.

$C_T$ means threshold cycle and signifies the cycle of a real-time PCR amplification assay in which signal from a reporter indicative of amplicons generation first becomes detectable above background. Because empirically measured background levels can be slightly variable, it is standard practice to measure the $C_T$ at the point in the reaction when the signal reaches 10 standard deviations above the background level averaged over the 5-10 preceding thermal cycles.

DETAILED DESCRIPTION

The present invention relates to compositions and methods for nucleic acid based diagnostic assays. In particular, the present invention provides primers for symmetric PCR, asymmetric PCR, and other amplification modalities. In some embodiments, the present invention provides multiple primers for amplification of related nucleic acid targets in a single reaction.

Embodiments of the present invention find use in the detection of multiple strains, variants, subtypes, etc. of the same microorganism or homologs or orthologs of prokaryotic or eukaryotic organisms. By using a series of primers with different levels of homology to the target sequences, embodiments of the present invention provide compositions and methods for performing such detection reactions in a single reaction vessel. The compositions and methods described herein find use in a variety of research, diagnostic, and screening applications.

I. Asymmetric PCR

In some embodiments, the present invention provides primers for use in amplification and detection assays. The methods described herein are not limited by the type of amplification that is employed. In certain embodiments, asymmetric PCR is employed, such as LATE-PCR.

PCR is a repeated series of steps of denaturation, or strand melting, to create single-stranded templates; primer annealing; and primer extension by a thermally stable DNA polymerase such as *Thermus aquaticus* (Taq) DNA polymerase. A typical three-step PCR protocol (see Innis et al., Chapter 1) may include denaturation, or strand melting, at 93-95° C. for more than 5 sec, primer annealing at 55-65° C. for 10-60 sec, and primer extension for 15-120 sec at a temperature at which the polymerase is highly active, for example, 72° C. for Taq DNA polymerase. A typical two-step PCR protocol may differ by having the same temperature for primer annealing as for primer extension, for example, 60° C. or 72° C. For either three-step PCR or two-step PCR, an amplification involves cycling the reaction mixture through the foregoing series of steps numerous times. During the course of the reaction the times and temperatures of individual steps in the reaction may remain unchanged from cycle to cycle, or they may be changed at one or more points in the course of the reaction to promote efficiency or enhance selectivity. In addition to the pair of primers and target nucleic acid a PCR reaction mixture typically contains each of the four deoxyribonucleotide 5' triphosphates (dNTPs) at equimolar concentrations, a thermostable polymerase, a divalent cation, and a buffering agent. A reverse transcriptase is included for RNA targets, unless the polymerase possesses that activity. The volume of such reactions is typically 25-100 µl. Multiple target sequences can be amplified in the same reaction. In the case of cDNA amplification, PCR is preceded by a separate reaction for reverse transcription of RNA into cDNA, unless the polymerase used in the PCR possesses reverse transcriptase activity. The number of cycles for a particular PCR amplification depends on several factors including: a) the amount of the starting material, b) the efficiency of the reaction, and c) the method and sensitivity of detection or subsequent analysis of the product. Cycling conditions, reagent concentrations, primer design, and appropriate apparatuses for typical cyclic amplification reactions are well known in the art (see, for example, Ausubel, F. Current Protocols in Molecular Biology (1988) Chapter 15: "The Polymerase Chain Reaction," J. Wiley (New York, N.Y. (USA)).

Ideally, each strand of each amplicon molecule binds a primer at one end and serves as a template for a subsequent round of synthesis. The rate of generation of primer extension products, or amplicons, is thus generally exponential, theoretically doubling during each cycle. The amplicons include both plus (+) and minus (−) strands, which hybridize to one another to form double strands. To differentiate typical PCR from variations described herein, typical PCR is referred to as "symmetric" PCR. Symmetric PCR thus results in an exponential increase of one or more double-stranded amplicon molecules, and both strands of each amplicon accumulate in equal amounts during each round of replication. The efficiency of exponential amplification via symmetric PCR eventually declines, and the rate of amplicon accumulation slows down and stops. Kinetic analysis of symmetric PCR reveals that reactions are composed of: a) an undetected amplification phase (initial cycles) during which both strands of the target sequence increase exponentially, but the amount of the product thus far accumulated is below the detectable level for the particular method of detection in use; b) a detected amplification phase (additional cycles) during which both strands of the target sequence continue to increase in parallel and the amount of the product is detectable; c) a plateau phase (terminal cycles) during which synthesis of both strands of the amplicon gradually stops and the amount of product no longer increases. Symmetric reactions slow down and stop because the increasing concentrations of complementary amplicon strands hybridize to each other (reanneal), and this out-competes the ability of the separate primers to hybridize to their respective target strands. In addition, large amounts of double stranded DNA may inhibit the extension activity of polymerases. Typically reactions are run long enough to guarantee accumulation of a detectable amount of product, without regard to the exact number of cycles needed to accomplish that purpose.

A technique that has found limited use for making single-stranded DNA directly in a PCR reaction is "asymmetric PCR." Gyllensten and Erlich, "Generation of Single-Stranded DNA by the polymerase chain reaction and its application to direct sequencing of the HLA-DQA Locus," Proc. Natl. Acad. Sci. (USA) 85: 7652-7656 (1988); Gyllensten, U. B. and Erlich, H. A. (1991) "Methods for generating single stranded DNA by the polymerase chain reaction" U.S. Pat. No. 5,066,584, Nov. 19, 1991; all of which are herein incorporated by reference. Asymmetric PCR differs from symmetric PCR in that one of the primers is added in limiting amount, typically $1/100$th to $1/5$th of the concentration of the other primer. Double-stranded amplicon accumulates during the early temperature cycles, as in symmetric PCR, but one primer is depleted, typically after 15-25 PCR cycles, depending on the number of starting templates. Linear amplification of one strand takes place during subsequent cycles utilizing the undepleted primer. Primers used in asymmetric PCR reactions reported in the literature, including the Gyllensten patent, are often the same primers known for use in symmetric PCR. Poddar (Poddar, S. (2000) "Symmetric vs. Asymmetric PCR and Molecular Beacon Probe in the Detection of a Target Gene of Adenovirus," Mol. Cell. Probes 14: 25-32 compared symmetric and asymmetric PCR for amplifying an adenovirus substrate by an end-point assay that included 40 thermal cycles. He reported that a primer ratio of 50:1 was optimal and that asymmetric PCR assays had better sensitivity that, however, dropped significantly for dilute substrate solutions that presumably contained lower numbers of target molecules. In some embodiments, asymmetric PCR is used with embodiments of the assays described herein.

In certain embodiments, an amplification method is used that is known as "Linear-After-The Exponential PCR" or, for short, "LATE-PCR." LATE-PCR is a non-symmetric PCR method; that is, it utilizes unequal concentrations of primers and yields single-stranded primer-extension products, or amplicons. LATE-PCR includes innovations in primer design, in temperature cycling profiles, and in hybridization probe design. Being a type of PCR process, LATE-PCR utilizes the basic steps of strand melting, primer annealing, and primer extension by a DNA polymerase caused or enabled to occur repeatedly by a series of temperature cycles. In the early cycles of a LATE-PCR amplification, when both primers are present, LATE-PCR amplification amplifies both strands of a target sequence exponentially, as occurs in conventional symmetric PCR. LATE-PCR then switches to synthesis of only one strand of the target sequence for additional cycles of amplification. In certain real-time LATE-PCR assays, the limiting primer is exhausted within a few cycles after the reaction reaches its $C_T$ value, and in certain assays one cycle after the reaction reaches its $C_T$ value. As defined above, the $C_T$ value is the thermal cycle at which signal becomes detectable above the empirically determined background level of the reaction. Whereas a symmetric PCR amplification typically reaches a plateau phase and stops generating new amplicons by the 50th thermal cycle, LATE-PCR amplifications do not plateau and continue to generate single-stranded amplicons well beyond the 50th cycle, even through the 100th cycle. LATE-PCR amplifications and assays typically include at least 60 cycles, preferably at least 60 cycles when small (100 or less) numbers of target molecules are present at the start of amplification.

With certain exceptions, the ingredients of a reaction mixture for LATE-PCR amplification are generally the same as the ingredients of a reaction mixture for a corresponding symmetric PCR amplification. The mixture typically includes each of the four deoxyribonucleotide 5' triphosphates (dNTPs) at equimolar concentrations, a thermostable polymerase, a divalent cation, and a buffering agent. As with symmetric PCR amplifications, it may include additional ingredients, for example reverse transcriptase for RNA targets. Non-natural dNTPs may be utilized. For instance, dUTP can be substituted for dTTP and used at 3 times the concentration of the other dNTPs due to the less efficient incorporation by Taq DNA polymerase.

In certain embodiments, the starting molar concentration of one primer, the "Limiting Primer," is less than the starting molar concentration of the other primer, the "Excess Primer." The ratio of the starting concentrations of the Excess Primer and the Limiting Primer is generally at least 5:1, preferably at least 10:1, and more preferably at least 20:1. The ratio of Excess Primer to Limiting Primer can be, for example, 5:1 . . . 10:1, 15:1 . . . 20:1 . . . 25:1 . . . 30:1 . . . 35:1 . . . 40:1 . . . 45:1 . . . 50:1 . . . 55:1 . . . 60:1 . . . 65:1 . . . 70:1 . . . 75:1 . . . 80:1 . . . 85:1 . . . 90:1 . . . 95:1 . . . or 100:1 . . . 1000:1 . . . or more. Primer length and sequence are adjusted or modified, preferably at the 5' end of the molecule, such that the concentration-adjusted melting temperature of the Limiting Primer at the start of the reaction, $T_M[0]^L$, is greater than or equal (plus or minus 0.5° C.) to the concentration-adjusted melting point of the Excess Primer at the start of the reaction, $T_M[0]^X$. Preferably the difference $(T_M[0]^L - T_M[0]^X)$ is equal to or greater than 0, preferably at least +3, and more preferably the difference is at least +5° C.

Amplifications and assays according to embodiments of methods described herein can be performed with initial reaction mixtures having ranges of concentrations of target molecules and primers. LATE-PCR assays are particularly suited for amplifications that utilize small reaction-mixture volumes and relatively few molecules containing the target sequence, sometimes referred to as "low copy number." While LATE-PCR can be used to assay samples containing large amounts of target, for example up to $10^6$ copies of target molecules, other ranges that can be employed are much smaller amounts, from to 1-50,000 copies, 1-10,000 copies and 1-1,000 copies. In certain embodiments, the concentration of the Limiting Primer is from a few nanomolar (nM) up to 200 nM. The Limiting Primer concentration is preferably as far toward the low end of the range as detection sensitivity permits.

As with PCR, either symmetric or asymmetric, LATE-PCR amplifications include repeated thermal cycling through the steps of strand melting, primer annealing and primer extension. Temperatures and times for the three steps are typically, as with symmetric PCR, 93-95° C. for at least 5 sec for strand melting, 55-65° C. for 10-60 sec for annealing primers, and 72° C. for 15-120 sec for primer extension. For 3-step PCR amplifications, primer annealing times are generally in the range of 10-20 sec. Variations of temperature and time for PCR amplifications are known to persons skilled in the art and are generally applicable to LATE-PCR as well. For example, so-called "2-step" PCR, in which one temperature is used for both primer annealing and primer extension, can be used for LATE-PCR. In the case of "2-step" reactions the combined annealing-extension step can be longer than 30 sec, but preferably as short as possible and generally not longer that 120 sec.

Design of primer pairs for use in LATE-PCR can be performed directly, as will be explained. Alternatively, it can begin with selecting or designing a primer pair for symmetric PCR by known methods, followed by modifications for LATE-PCR. In general, symmetric PCR primers are designed to have equal melting points at some set of standard conditions of primers concentration and salt concentration. Symmetric PCR primers are conveniently designed and analyzed utilizing an available computer program. For symmetric and asymmetric PCR the standard techniques for calculating melting temperatures $(T_M)$ have been the "Nearest Neighbor" method and the "2(A+T)+4 (G+C)" method. As discussed above, $T_M[1]$ which is the $T_M$ of the primer at a standard primer concentration of 1 uM and 0.07M salt (monovalent cations). Conversion from the $T_M$ given by a typical computer program to $T_M[1]$ generally has minimal effect on the relationship of the $T_M$'s of a primer pair. For the concentration-adjusted melting temperatures of primer pairs in embodiments described herein, either actual measurement or an appropriate calculation using the Nearest Neighbor method is generally required.

In practice, once a particular target sequence (for instance a sequence flanking a mutation within a gene) has been chosen for amplification, several candidate pairs of equal $T_M$ primers are designed via a computer program such as Visual OMP. The candidate primer pairs can then be scrutinized on the basis of additional criteria, such as possible primer-dimer formation, that are known in the art to cause non-desirable primer qualities. Satisfactory pairs of candidate primers are further scrutinized using software such as "BLAST" for possible non-specific matches to DNA sequences elsewhere in the known genome from the species of the target sequence (Madden, T. L. et al. (1996) "Applications of Network BLAST Server," Meth. Enzymol. 266: 131-141). Primers pairs are then compared as to their $T_M[0]$ values at several different possible concentrations and ratios such that the primer chosen to be the Limiting Primer will have an equal or greater $T_M[0]$ relative to the primer chosen to be the Excess Primer. In addition, pairs of candidate primers are examined in relation to the sequence of the amplicon they are expected to generate. For instance, certain target sequences may contain a GC-rich sequence at one end and a less GC-rich sequence at the other end. Where that occurs, choosing the Limiting Primer sequence within sequences at the GC-rich end will assist in achieving a higher melting point for the Limiting Primer relative to the Excess Primer, which will consist of sequences in the less GC-rich end. Examination of the candidate primer pairs relative to the amplicon sequence may suggest additional or different ways of modifying the sequences of one or both members of the pair, such as deliberately increasing or decreasing the length of the primer, most preferably at its 5' end, or introducing changes in base sequences within the primer which deliberately cause it to mismatch with its target in small regions. Such changes will increase or decrease the $T_M[0]$ of either the Limiting or Excess primer.

II. Design and Use of Thermodynamic Consensus Primers

In some embodiments, targets with different sequences are amplified by a consensus primer that is at least partially complementary to each of those sequences. That primer may be paired with a second primer that is fully complementary to all targets, or may be partially complementary to some of its targets. In some embodiments, the primers are used at the same concentration in symmetric PCR. In other embodiments, a consensus primer is used as either a limiting or excess primer in asymmetric PCR (e.g., LATE-PCR). In other embodiments, the consensus primer is used with other amplification methods, for example, isothermal amplifications.

In some embodiments of the present invention, the consensus primer is a "thermodynamic consensus primer"

designed to minimize the differences in melting temperatures of the different targets to the primer. This design contrasts to the currently used consensus primer design in which the complement of the most common target nucleotide is chosen for primer. That method can result in the selection of primer sequences that hybridize some targets with very low $T_M$, which can delay or prevent the amplification and detection of those targets. In contrast, a thermodynamic consensus primer reduces the differences in the ability of the primer to hybridize with different target sequences and initiate amplification. Although some available programs for the design of consensus primers, such as PrimerHunter (Duitama, J. et al (2009) "PrimerHunter: a primer design tool for PCR-based virus subtype identification" *Nucleic Acids Res.* 37, 2483-92) allow the selection of a minimum $T_M$ for the primer with each possible target, those programs still select primer nucleotides that are complementary to the majority of targets, as long as the $T_M$ remains above the minimum. Embodiments of the present invention provide a series of steps that keeps the $T_M$ difference low, without specifying $T_M$ maximum and $T_M$ minimum beforehand. It also takes into account the $T_M$ of the primer with the amplicon (e.g., the fully-complementary target).

A thermodynamic consensus primer can have advantages for amplification of a variable sequence target compared with the use of a target-specific primer, a degenerate primer, or a consensus primer designed primarily on a most-common-nucleotide method, even if the set of possible targets vary by only a single nucleotide over the position hybridized by the primer. Those advantages increase as the number of variable nucleotides increases. The thermodynamic consensus primer design is therefore particularly useful in situations where the set of possible targets vary at 4 or more nucleotide positions over the position hybridized by the primer, and in cases where the set of possible targets vary at 6 or more nucleotides over the position hybridized by the primer.

The use of alternative nucleotides such as inosine that can effectively hybridize with different nucleotides is possible in the thermodynamic consensus primer design, but the use of such base can lower the $T_M$ of the primer to the amplicon, relative to the choice of one of the standard nucleotides. Therefore, it is preferred to limit such alternative nucleotides to one per primer and more preferred to use only standard nucleotides. Degenerate primers are essentially multiple primers used in combination and are not included in the definition of a consensus primer, even if some of the single nucleotide sites of the degenerate primers hybridize to the multiple targets with minimal $T_M$ differences.

Steps in the design of a thermodynamic consensus primer may include, for example: (1) the identification of one or more regions that could be targeted by the primer; (2) the choice of primer nucleotides for variable target nucleotides toward the 3' end of the primer (approximately one third of the total length) such that mismatched targets will hybridize to the primer with the least destabilization (e.g., will lower the overall $T_M$ by the fewest degrees); (3) selection of nucleotides over the remaining length of the primer that also minimize the number of destabilizing mismatches, but allow a small number of those mismatches if the $T_M$ of the primer to some targets would be reduced well below that with other targets (e.g., select nucleotides complementary to targets that are mismatched to the primer at other locations); and (4) choosing the overall primer length and, in some cases, specifying nucleotides at the 5' end of the primer such that the $T_M$ to the fully complementary target (e.g., the amplicon) is at the desired level for efficient amplification. In some embodiments, primers previously chosen to amplify at least one of the targets are modified using steps (2) through (4) in order to minimize primer to target $T_M$ differences. In such cases, it may also be useful to shorten or lengthen the primer to achieve the desired $T_M$ of the primer to particular targets and/or the fully complementary amplicon.

In some embodiments, the location of a thermodynamic consensus primer is chosen from a list of primer candidates selected using available primer design software. At least 2 nucleotides, preferably at least 3 nucleotides, and more preferably at least 4 nucleotides at the 3' end of the primer are generally complementary to all potential targets. Mismatches of any target near the 3' end of the primer are generally chose to be minimally destabilizing, for example, using an Inosine base in the primer, or choosing a nucleotide pairing such as G and T that has a low decrease in stability relative to the complementary nucleotides. The relative stability of nucleotide mismatches is available in SantaLucia and Hicks (2004) "The Thermodynamics of DNA Structural Motifs", *Annu. Rev. Biophys. Biomol. Struct.* 33:415-40, which is incorporated herein by reference. Toward the center third of the primer, or in the third of the primer toward the 5' end, a few nucleotides can be selected that are complementary to targets that are poorly matched at other locations of the primer, even if those nucleotides are more destabilizing to some targets. This is done to minimize the $T_M$ difference between the primer and each of the targets. In some embodiments, an A or T nucleotide is chosen in such cases, so that the $T_M$ of the primer to each target will not be too far below the $T_M$ with the fully complementary amplicon. Destabilizing mismatches may be chosen near the 5' end of the primer with relatively minor impact on $T_M$.

Thermodynamic consensus primers follow generally accepted primer design criteria, including typical ranges and distributions of GC content, absence of extensible 3' homodimers or heterodimers, and $T_M$ compatibility with paired primers and other primers within a multiplex amplification.

III. Multiple Primers for Amplification Reactions

In some embodiments, the present invention provides compositions and methods that utilize multiple primers with similar sequences at different concentrations in a single amplification reaction in order to amplify one or more targets from a wide range of related nucleic acid targets (e.g., from different strains of a bacteria or virus, or highly conserved genes from a variety of organisms) or to identify an unknown member of a known class or microorganism or gene.

Existing assays for variable sequences may be limited to a narrow range of sequence variation and can fail to amplify particular strains. The use of "degenerate primers" has been one past solution used with symmetric PCR, but risks low efficiency or failure due to the very small concentrations of each particular primer that is included in the mix. The primer-target hybridization thermodynamics (including melting temperature) are not typically (if ever) considered in the design of degenerate primers or consensus primers.

In some embodiments, the present invention addresses these shortcomings by providing compositions and methods that utilize a) a first primer and b) a plurality of second primers. In some embodiments, the first primer is present in excess (e.g., 5 to 100 times the level of the second primer). In some embodiments, the first primer is completely complementary to all of the target sequences to be amplified.

In other embodiments, the first primer is partially complementary, but is able to hybridize to and initiate amplification of most or all target sequences under the conditions (e.g., salt concentrations and annealing temperature) used during the amplification reaction. In still other embodiments, additional, sequence-related first primers that either partially or completely match a subset or individual members of the family of targets are included in the reaction mixture, either at the same concentration or at lower concentrations.

In some embodiments, the plurality of second primers comprises one or more primers that either partially or completely match a subset or individual members of the family of targets. The second primer(s) are generally designed to hybridize to the regions of the target sequences that differ in sequence. In some embodiments, the second primer is one consensus primer that partially matches each of the target sequences and is able to hybridize to all of the target sequences to be analyzed. In some embodiments, a plurality of sequence-related limiting primers (e.g., intermediate primers that partially match one or more (but not the entire set) of target sequences) are utilized. In some embodiments, the second primers comprise a primer that exactly matches each of the target sequences. In some embodiments, one or more intermediate primers are combined with one or more exactly matching primers. In some embodiments, the second primers are present at a lower concentration (e.g., 5 to 100-fold lower) that that of the first primer. In some embodiments, some of the second primers are used at lower concentrations than other second primers.

As described, embodiments of the present invention utilize intermediate primers that hybridize to one target sequence or group of target sequence better than the other. The present invention is not limited to a particular method or altering a primer's ability to hybridize to a target sequence or group of target sequences. For example, in some embodiments, primers vary in sequence, base composition, presence or absence of modified or non-standard bases, etc. In some embodiments, a plurality of primers intended to amplify one or more targets from a range of related nucleic acid targets may include primers partially homologous oligonucleotide sequences, ranging from about 50% homology to about 98% homology. In some embodiments, up to three, preferably up to two, and more preferably one of the partially homologous primers are used at a concentration at least 5 times higher than one or more other partially homologous primers, preferably at least 10 times higher than other partially homologous primers. The primers used at higher concentrations in such a set may be each specific to one target sequence, or may be any consensus sequence including a thermodynamic consensus sequence.

In some embodiments, the compositions and methods described herein find use in asymmetric PCR (e.g., LATE PCR). In some embodiments, the compositions and methods find use in symmetric or "standard" PCR. Amplified target sequences may be identified using any suitable method, including but not limited to, hybridization with a labeled probe, sequencing or direct detection via gel electrophoresis and staining of nucleic acids.

The present invention is not limited to detection of particular target sequences. Embodiments of the present invention find use in the detection of a variety of target sequences including, but not limited to, variants of genes, homologs of genes, orthologs of genes, or subtypes of genes. Exemplary genes include, but are not limited to genes from pathogenic agents (e.g., viruses, bacteria, or fungi), animals (e.g., humans, livestock, or companion animals), or other organisms of interest.

The compositions and methods described herein find use in a variety of research, clinical, and screening applications.

Examples include, but are not limited to, identification of unknown strains of microorganisms or homologs/orthologs of genes, drug screening (e.g., screening for growth of microorganism or expression of particular genes), epidemiological applications (e.g., monitoring emergence of new strains of pathogens and monitoring spread of disease), etc.

IV. Kits and Systems

In some embodiments, the present invention provides kits, systems, and software for use in performing the described methods. For example, in some embodiments, kits and systems comprise primers (e.g., as described above), reagents for performing amplification reactions, instruments (e.g., thermocyclers and detection instruments), and software for analyzing data, generating melting curves, and displaying results.

In some embodiments, instruments are automated and include all the hardware and software necessary for performing and analyzing samples (e.g., robotics, thermocyling capabilities, detection capabilities, software and computer processors for analyzing data, and a display for displaying results).

In some embodiments, reagents are provided as a reagent pack that includes all of the reagents necessary, sufficient, or useful for performing a detection assay (e.g., reagents for isolating nucleic acids from samples, reagents for performing amplification reactions, and reagents for detection of amplification products). In some embodiments, reagents are provided in a reagent pack. In some embodiments, the reagent pack comprises individual compartments for each reagent (e.g., buffers, primers, probes, controls, enzymes, detection reagents, etc.). In some embodiments, the reagent pack comprises magnetic beads. In some embodiments, the reagent pack comprises empty compartments for mixing of reagents and waste disposal.

EXAMPLES

The following Examples are presented in order to provide certain exemplary embodiments of the assays described herein and are not intended to limit the scope thereof.

Example 1

Design of a Thermodynamic Consensus Primer

Several sequences from the 1D gene (encoding coat protein VP1) of foot and mouth disease virus (FMDV), Asia 1 serotype strains, were obtained from GenBank and were aligned using the ClustalW2 program available on the European Bioinformatics Institute website. A region of moderate variability within this highly variable gene was selected for the design of a limiting primer using LATE-PCR criteria that could be used as a consensus primer to amplify the sequences for the first 8 strains shown in FIG. 4. The ninth strain, BR/Myanmar 001-2006, was not included in the consensus design, but was used subsequent to the design to test the limits of amplification. Sequences of this region of the 1D gene in strains of non-Asia 1 serotypes show low sequence identity and their amplification using this consensus primer is not anticipated. For purposes of discussion and testing, viral sequences are shown as DNA nucleotides. Testing viral RNA sequences utilizes the synthesis of complementary DNA (cDNA) strand using techniques that are well known to those skilled in the art.

The two nucleotides, positions 31 and 32 in FIG. 4, at the 3' end of the primers were homologous among all Asia-1 serotype strains available in Genbank and therefore could hybridize to that location of a complementary DNA strand.

Position 30 in the viral sequence was an A or G depending on the specific strain. The G nucleotide was chosen at this position of the primer, as the G in the primer mismatched to a T in some cDNA targets is far less destabilizing than an A in the primer mismatched to a C in other cDNA targets. The former situation allows hybridization and extension of mismatched targets, while the latter would provide very limited opportunity for hybridization and extension of the mismatched targets.

The T nucleotide in the primer at nucleotide 21 was also chosen to avoid a highly destabilizing C to A mismatch (to the IND 82-96 target) that would occur if the more prevalent C was used in the primer. The choice of the T minimizes the difference in $T_M$ between the primer and the targets with nucleotide variation at that location. A similar choice of a T was made at nucleotide 16, although in this case it was the more common variation.

The G nucleotide was chosen for nucleotide 15 to avoid the more destabilizing mismatches involving a C (either in the primer or target). The G to A and G to G mismatches are moderately destabilizing. The selection of the T at nucleotide 9 allows a destabilizing T to C mismatch with strain 3kimron, but the hybrid has only one other (minor) mismatch at position 21 and the $T_M$ with the consensus primer is at the upper range among all targets. C was chosen at nucleotide 6 and at nucleotide 2 of the primer, even though destabilizing mismatches result with strain IND 324-98 and strain TNN 14-93 respectively. Alternative choices at nucleotide 6 would increase the $T_M$ of the primer to the former target, but would substantially lower the $T_M$ of the primer to the latter target. Choosing an A for nucleotide 2 of the primer would increase the $T_M$ of the primer to the TNN 14-93 target only slightly, but would drop the $T_M$ of the primer to the IND 324-98 target and all other tested targets. Thus, nucleotides that were complementary to those targets at one of the two sites were chosen, rather than choosing a moderately destabilizing mismatch at both sites.

The $T_M$ of the thermodynamic consensus primer at 50 nM to each of the 8 targets ranges between 60 and 70 degrees, which is within 4 to 14 degrees of the primer $T_M$ with the complementary target. Once the consensus primer is extended on any of the targets, the complementary target is synthesized by extension of a paired (excess) primer.

Example 2

Amplification of Different Synthetic DNA Targets Using Matched and Consensus Limiting Primers for the Foot-and-mouth Disease Virus (FMDV) 1D Gene This Example compares the use of different primers to amplify variants of the FMDV 1D gene. Each of several synthetic, single-stranded DNA oligonucleotides was amplified using a specific, complementary limiting primer for that target in some samples and a thermodynamic consensus limiting primer in other samples. The consensus limiting primer sequence was chosen to minimize the melting temperature ($T_M$) differences when possible rather than use the most common sequence. $T_M$ was predicted using Visual OMP (DNA Software). One target (shown below) contained 105 nucleotides complementary to segments of the positive strand RNA from the FMDV 1D to 2A/B genes of Asia1 serotype isolate IND 116-90 (GenBank accession # DQ989305). A portion of the FMDV sequence was not included in order to simplify oligonucleotide synthesis.

(SEQ ID NO: 1)
5'AGAAGAAGGGCCCAGGGTTGGACTCTGAGTGGTGTCAAGAGCTAGCA

AAGGCCTGGGGCAGTATGTCTCCGCGCGTTTCATGCGGATCAAAAGCTC

AGTGATGGT-3'.

Other targets contained the same sequence except for variations in the region hybridizing the limiting primer (shown above in bold type). That region of the other targets included nucleotides complementary to different FMDV Asia1 serotype isolates. Specific limiting primer DNA sequences, analogous to those RNA isolates are shown in FIG. 4. Thus, targets varied from one another only in the portion that hybridized with the limiting primers and were identical over the remaining nucleotides, including those matching the excess primer and those complementary to the probe. Specific limiting primers were designed to have a predicted $T_M$ of about 74 degrees with their complementary target at limiting primer concentration of 50 nM, potassium concentration of 50 mM, and magnesium concentration of 3 mM. Two target types (IND 82-96 and IND 324-98) were longer to include nucleotides complementary to specific primers. One target (3kimron iso61) included sequences that hybridized to the full length of the consensus primer, although the specific primer was only 27 nucleotides and did not include the boxed nucleotides in FIG. 4. The excess primer, 5'-AGGGCCCAGGGTTGGACTC-3' (SEQ ID NO:2) and probe, 5'-Cal Red 610-ATAGCTCTTGACAC-CACTCAT-Black Hole Quencher 2-3' (SEQ ID NO:3) were the same for all amplifications. The predicted $T_M$ of the excess primer at 1,000 nM to all target complements was 73.7° C. The predicted $T_M$ of the probe at 500 nM to all targets was 61.9° C.

Samples included 1×PCR buffer (Platinum Tfi reagent, Invitrogen), 3 mM MgCl$_2$, 400 nM of each dNTP, 250 nM probe, 1000 nM excess primer, 50 nM limiting primers (consensus or one specific), 100 nM PrimeSafe 002 (an oligonucleotide with modified terminal nucleotides designed to reduce non-specific amplification), approximately 10,000 copies of one target type, and 2 Units Platinum Tfi DNA polymerase (Invitrogen) in a final volume of 25 microliters. Samples were placed in a Stratagene Mx3005P thermal cycler and were heated to 95° C. for 1 minute, followed by 20 cycles of 95° C. for 10 seconds, 68° C. for 30 seconds, then 40 cycles of 95° C. for 10 seconds, 68° C. for 30 seconds, and 58 degrees for 21 seconds with fluorescence detection.

The real-time PCR results for four of the targets are shown in FIG. 1. In each plot, fluorescence increase in triplicate samples using the limiting primer matched to a target is compared with that in triplicate samples using the consensus limiting primer. Use of the consensus limiting primer delayed reaching detection threshold relative to the use of a specific limiting primer, as measured by an increase in threshold cycle ($C_T$) values, with decreasing $T_M$ of the consensus primer to the target. The difference in mean $C_T$ values (delta $C_T$) between the use of a specific limiting primer and the consensus limiting primers for 8 targets is plotted in FIG. 2. That difference showed a linear increase as a function of decreasing $T_M$ of the consensus primer with a given target. Only the BR/Myanmar 001-2006 sequence target was not detected using the consensus limiting primer; the $T_M$ of the hybrid evidently being too low to initiate amplification under the conditions used. This experiment illustrates the use of LATE-PCR for the detection of variable sequences. Over 90% of this segment of VP1 gene sequences of FMDV serotype Asia-1 found in GenBank are detectable using this thermodynamic consensus limiting primer.

Example 3

Amplification of a Synthetic DNA Target Using the Consensus Limiting Primer in Combination with Low Concentrations of other Sequence-related Limiting Primers The target complementary to primer 8 (IND 324-98) was amplified using 50 nM specific limiting primer, or 50 nM consensus limiting primer, or a combination of 50 nM consensus limiting primer and 5 nM other limiting primers under conditions that were otherwise identical to those used in Example 1. The primer sequences and the concentration-adjusted $T_M$ of those primers to the target are shown in FIG. 5. The real-time fluorescence plots in FIG. 3 show that adding low concentrations of the sequence-related primers improved amplification of the target, reducing the number of cycles required to reach detection threshold. Table I quantifies those differences in terms of $C_T$ values. Using the consensus limiting primer alone (FIG. 3A) resulted in a mean $C_T$ value of 42.8. The delay compared with using 50 nM of the specific primer is due to only a fraction of the consensus primers hybridizing to and being extended on the target. However, once that initial extension takes place, even with a small percentage of the targets, the excess primer is able to copy that extension product and provide a target which is fully complementary to the consensus limiting primer for efficient amplification in subsequent cycles and detection threshold is eventually reached.

Adding 5 nM of the limiting primer specific for the target reduced the mean $C_T$ value to 40.8 (FIG. 3B), two cycles lower than that obtained using the consensus limiting primer alone. The predicted melting temperature of the specific limiting primer to its target is lower in this example due to the 10-fold lower concentration used. The specific limiting primer presumably amplifies the initial targets, providing additional targets for amplification by the consensus limiting primer during the early cycles of the reaction. Even though the initial amplification efficiency of all targets (initial and added copies) by the consensus primer is low, a higher number of targets is available for hybridization and extension of the consensus limiting primer and detection is earlier.

Adding 5 nM of one of the 3 other sequence-related limiting primers ("intermediate primers") lowered the mean $C_T$ value by 2.6 to 5.5 cycles relative to that obtained with the consensus limiting primer alone (FIG. 3C). The present invention is not limited to a particular mechanism. Indeed, an understanding of the mechanism is not necessary to practice the present invention. Nonetheless, it is contemplated that the intermediate primers amplify the initial targets and the resulting targets, now complementary to the intermediate primers, are more efficiently amplified by the consensus primer. The fact that the two intermediate primers (IND 23-95 and IND 339-96) are more similar in sequence to the consensus limiting primer than the other intermediate primer (IND 116-90) and resulted in the lower $C_T$ values provides additional evidence that generating targets that are more efficiently amplified by the consensus limiting primer provides a means of improving the overall amplification efficiency, thereby reaching detection at an earlier cycle.

Adding 5 nM of each of the 3 intermediate primers lowered the $C_T$ value by 7.3 cycles relative to that obtained with the consensus limiting primer alone (FIG. 3D). The present invention is not limited to a particular mechanism. Indeed, an understanding of the mechanism is not necessary to practice the present invention. Nonetheless, it is contemplated that this combination of primers provided a means to "step" the target incrementally toward a sequence more efficiently amplified by the consensus primer.

It is contemplated that targets of some strains, such as BR/Myanmar 001-2006, that are not amplified by a consensus limiting primer would be amplified by a combination of that primer plus a lower concentration of one or more intermediate primers. By designing an assay that includes a range of sequence-related primers, a wide-range of unknown targets can be amplified in a detection assay. This could be for different strains of a bacteria or virus sequence, as tested here, or for identifying more distantly related organisms through the amplification of a conserved gene.

It is also possible to use sequence-related primers at reduced concentrations for the excess primer in asymmetric PCR, or for both forward and reverse primers in symmetric PCR. In these cases the sequence-related primers may be used at higher concentrations than required for those used with limiting primers. An increase in non-specific amplification is more likely at higher total primer concentrations, so use of sequence-related primers with the limiting primer is preferred.

Lowering the concentration of primers lowers the $T_M$ and amplification efficiency. In some embodiments, primers to be used a very low concentrations are designed with higher $T_M$ by increasing their length. This design improves initial binding to target and increases the efficiency of generating the intermediate targets. Such longer primers are alternatively used at even lower concentrations (e.g., 100-fold below a consensus primer), keeping the total primer concentration low and reducing the likelihood of non-specific amplification. This type of design modification finds use, for example, in excess primer design or symmetric PCR, so that many sequence-related primers are used, but at concentrations that would not substantially increase the total primer concentration.

TABLE I

Results of target IND 324-98 detection using matched, consensus, and intermediate limiting primers.

| 50 nM Limiting Primer/strain | 5 nM Limiting Primer(s) | mean $C_T$ |
|---|---|---|
| IND 324-98 (matched) | none | 30.5 |
| Consensus primer (mis-matched) | none | 42.8 |
| Consensus primer | IND 324-98 (matched) | 40.8 |
| Consensus primer | IND 116-90 (intermediate) | 40.2 |
| Consensus primer | IND 23-95 (intermediate) | 37.8 |
| Consensus primer | IND 339-96 (intermediate) | 37.3 |
| Consensus primer | all 3 intermediate combined | 35.5 |

Example 4

Amplification of a Synthetic DNA Target Using a Thermodynamic Consensus Excess Primer in Combination with Low Concentrations of Sequence-related Primers Synthetic double stranded DNA targets with the sequences of different bacterial homologs were custom synthesized by Integrated DNA Technologies. A single limiting primer was used for all samples in this example. Since the genes in this example show variation within the region targeted by the limiting primer, it was designed as a thermodynamic consensus primer. The primer at 50 nM concentration had predicted $T_m$ of 75° C. and 71° C. with targets designated M1 and M2, respectively, and 79° C. with the fully complementary amplicon target.

Two gene-specific excess primers, one for target M1 and one for target M2 were designed to generate amplicons of 233 and 237 nucleotides when used in combination with the limiting primer described above. These "gene specific" excess primers were not completely complementary to the targets; the first included 1 mismatch to target M1 and the second included 2 mismatches to target M2. It is noted that fully complementary primers could be used similarly, but the above primers were chosen for the potential to amplify additional homologs not used in this example. The $T_m$ of the M1 excess primer at 1 µM concentration was 75° C. to the synthetic gene target and 76° C. to the fully complementary amplicon strand. The $T_m$ of the M2 excess primer at 1 µM concentration was 70° C. to the synthetic gene target and 76° C. to the fully complementary amplicon strand.

A 31-mer thermodynamic consensus excess primer was designed that was partially complementary to both targets. This primer and the M1 and M2 excess primers share the same 10 nucleotides at the 3' end and have similar $T_m$ (about 76° C.) to their fully complementary targets. However, due to the high variability of these targets, the mismatched consensus excess primer $T_m$ at a 1 µM concentration was only 48° C. with target M1 and 60° C. with target M2. Therefore, intermediate primers were designed that contained fewer mismatches to each of the targets and therefore a higher $T_m$. Intermediate primer 2a had 3 mismatches (G to T) to the M2 target. The primer length was 40 nucleotides in order to compensate for the lower concentration of 10 nM, only 1% that of the consensus primer. At that concentration, the predicted $T_m$ of primer 2a was 70° C. with target M2 and 78° C. with its fully complementary amplicon target. Note that the preferred design is for the $T_m$ of the intermediate primers no more than 2 degrees above that of the consensus primer to its fully complementary target, and the more preferred design is for the $T_m$ of the intermediate primers to be equal to or below that of the consensus primer to its fully complementary target. The use of intermediate primers with $T_m$ (to complements) above those limits is possible, but risks increasing the amount of non-specific amplification.

Three intermediate primers were designed to step the M1 target sequence to the thermodynamic consensus excess primer. Primer 1a was a 43-mer with 3 mismatches to that target with a $T_m$ of 70° C. at the 10 nM primer concentration. A 40-mer primer 1b, although more highly mismatched to the M1 target, had only one mismatch to the complement of primer 1a and a $T_m$ of 70° C. to that amplification product at the 10 nM primer concentration. Similarly, 40-mer primer 1c targeted the amplification product that was the complement of primer 1b, having only 1 mismatch and a $T_m$ of 73° C. at the 10 nM primer concentration. The thermodynamic consensus excess primer, at a concentration of 1 µM, is able to hybridize with the complement of primer 1c with a $T_m$ of 73° C. Thus, amplification efficiency should be greatly increased after the 1c complement is generated during early amplification. (The $T_m$ of the consensus excess primer to the 1a and 1b complements are 58° C. and 67° C., respectively, so although extension of that primer directly from hybridization to those targets is possible, it would occur at a much lower frequency.)

Figure 6:
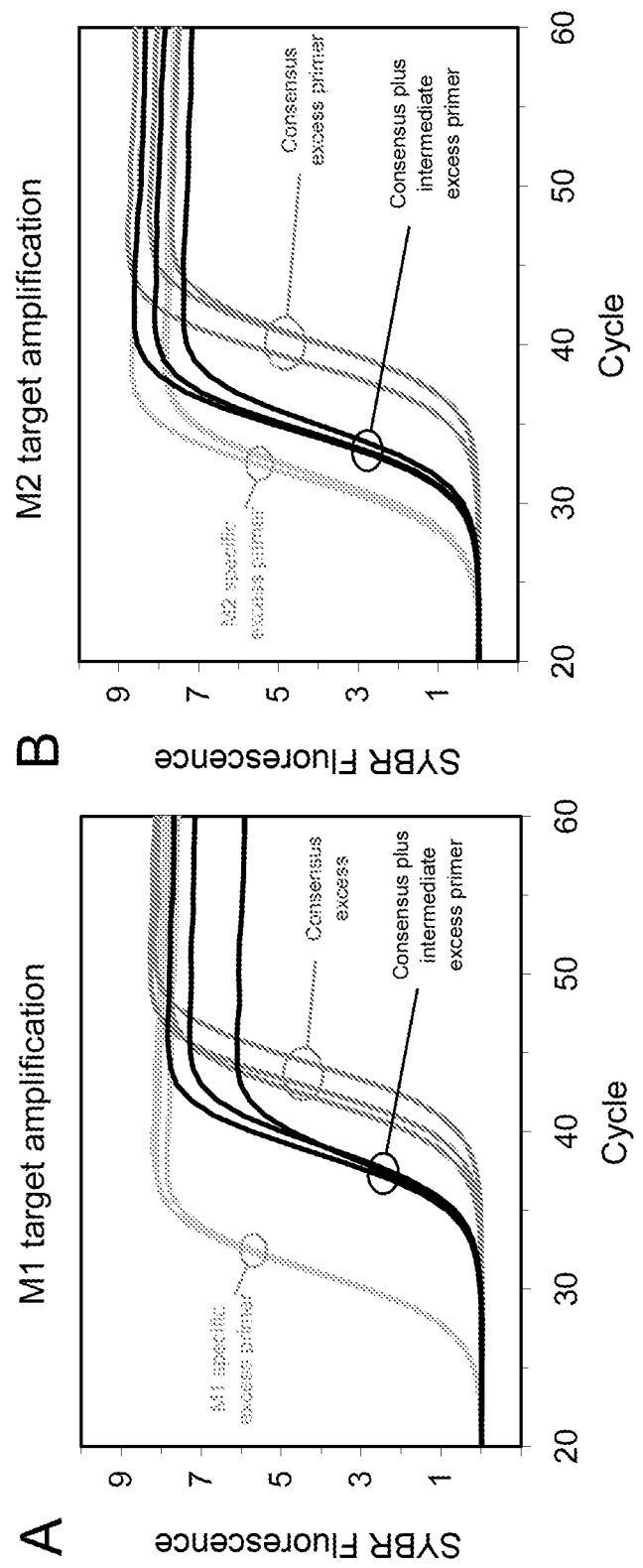

The results of amplification of the M1 and M2 targets (estimated 10,000 plasmid targets/sample) with different excess primers are shown in FIG. 6. The figure shows the increase in fluorescence of SYBR Green, a double-stranded DNA binding dye during real-time detection. The dye binds to all double stranded DNA, including non-specific product, so the presence of specific product was confirmed in all cases by the post-PCR melting analysis of both SYBR Green and hybridization probe fluorescence (data not shown). The efficiency of double-strand DNA amplification (i.e., the early phase of asymmetric PCR) is higher in samples displaying fluorescence increase at earlier cycles in the reaction and is quantified as mean threshold cycle ($C_T$) values in Table II. Samples with gene specific excess primers showed the highest efficiency; mean $C_T$ values were around 27 for each primer with its corresponding target. The thermodynamic consensus excess primer generated specific product in all three replicate samples for each target M1 and M2, but with much higher $C_T$ values. Although the high $C_T$ values indicate a low initial amplification efficiency, the amplification does occur using this design despite predicted $T_m$ with the targets M1 and M2 of 48° C. and 60° C., respectively, even with an annealing/extension temperature of 72° C. for a duration of 1 minute. As anticipated, using the intermediate primers with the consensus excess primer to amplify particular targets increased the amplification efficiency, as evidenced by a reduction in the mean $C_T$ values relative to samples with only the consensus excess primer. These results demonstrate the power of the thermodynamic consensus primer design for amplification of partially homologous targets and the ability of low concentrations of intermediate primers to improve the efficiency of the amplification. It is likely that inclusion of additional intermediate primers could improve the efficiency even further. For example, using additional intermediate primers with only one and two mismatches to target M1 (primer 1a had 3 mismatches) should improve that initial amplification steps. Such use of additional intermediate primers is likely to be advantageous for amplification in samples with low numbers of target molecules.

Example 5

Comparisons of Asymmetric PCR for Generating Single-stranded Products Using Multiple Gene-specific Primers vs. Thermodynamic Consensus Primers with or without Low Concentrations of Sequence-related Primers The M1 and M2 targets described above, as well as homologs M3, M4, and M5 were each amplified using 3 different asymmetric PCR methods with primers for detecting any one of the targets. Such assays are useful for identifying unknown bacterial or viral strains, or other gene variation. The first assay contains 3 limiting primers, each at a concentration of 50 nM, and 3 excess primers each at a concentration of 1 µM. Those primers are each designed to amplify sets of homologous targets. Each of the 5 targets in this example had a $T_m$ with at least one of the limiting primers in the range of 71° C. to 75° C. and a $T_m$ with at least one excess primer in the range of 70° C. to 75° C. Each limiting primer has a $T_m$ of about 79° C. to its fully complementary amplicon and each excess primer has a $T_m$ of about 76° C. to its fully complementary amplicon.

The second assay uses a single thermodynamic consensus limiting primer (different from that in Example 4) at a concentration of 50 nM and a single thermodynamic consensus excess primer at 1 µM. The consensus limiting primer has a $T_m$ with the 5 targets that ranges from 63° C. to 75° C., and a $T_m$ with the fully complementary amplicon of 79° C. The consensus excess primer has a $T_m$ with the 5 targets that ranges from 48° C. to 72° C., and a $T_m$ with the fully complementary amplicon of 76° C.

The third assay uses the same thermodynamic consensus limiting and excess primers at 50 nM and 1 µM, respectively, plus additional primers with homology to the limiting primer each at a concentration of 5 nM and additional primers with homology to the excess primer each at a concentration of 10 nM. The low concentration, "intermediate" primers are designed with greater complementarity to individual targets compared with that of the consensus primers in order to improve amplification efficiently, using the method described in the examples above.

All 3 assays used the same concentrations of other reagents (magnesium, dNTPs, Taq, etc.) and the same 2 step amplification with 60 cycles of annealing and extension at 72° C. for 1 minute and denaturation at 96 degrees for 10 seconds. Amplification of double-stranded DNA was monitored in real time using SYBR Green. Immediately following PCR, temperature was slowly lowered from 72° C. to 25° C. and the hybridization of a mismatch-tolerant, hybridization probe modified with Cal Orange fluorophore and Black Hole Quencher 1 was monitored. The annealing profile verifies amplification of the correct target, as each target has a unique sequence in the region hybridized by the probe.

Figure 7:
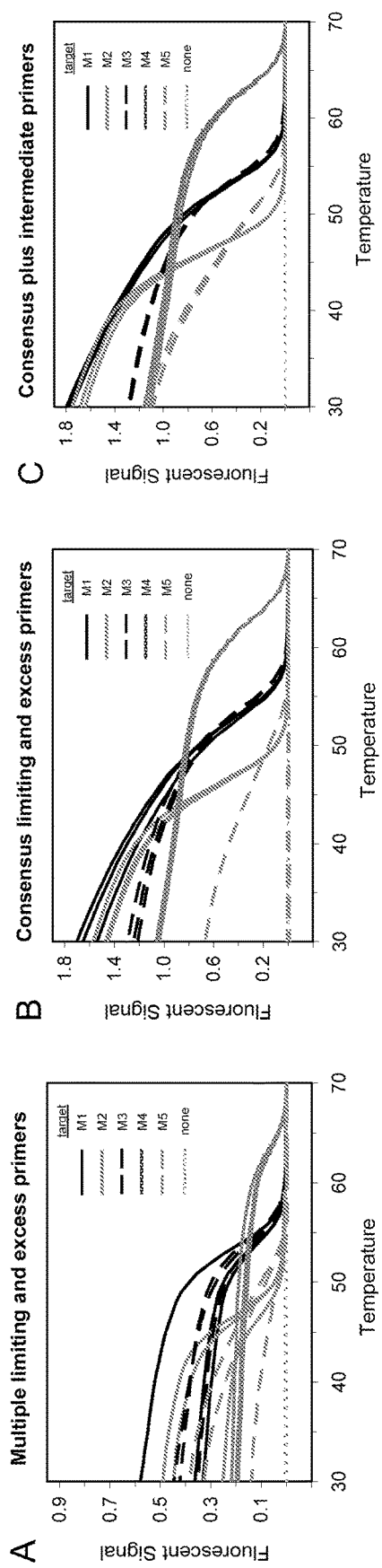

The results of the post-PCR hybridization is shown in FIG. 7. The assay containing multiple limiting and multiple excess primers generated the lowest fluorescent signals from the probe, reflecting a relatively low level of single-stranded specific product at the end of PCR (FIG. 7A), even though SYBR Green $C_T$ values were the lowest of the 3 assay methods (Table III), suggesting high double strand DNA amplification efficiency.

TABLE II

SYBR Green detection of synthetic target amplification using specific, consensus, and intermediate excess primers.

| Gene target | Mean $C_T$ values (SYBR fluorescence) of replicates amplified using: | | | |
|---|---|---|---|---|
| | Specific Excess Primer | Consensus Excess Primer | Consensus + Intermediate Primers | Change with Intermediate Primers |
| M1 | 26.6 | 38.5 | 34.3 | 4.2 |
| M2 | 27.2 | 35.2 | 30.1 | 5.1 |

TABLE III

SYBR Green detection of synthetic target amplification using multiple specific primers, or consensus primers with or without multiple intermediate primers.

| Gene target | Mean $C_T$ values (SYBR fluorescence) of replicates amplified using: | | | |
|---|---|---|---|---|
| | Multiple Specific Primers | Consensus Primers Only | Consensus + Intermediate Primers | Change with Intermediate Primers |
| M1 | 26.8 | 38.1 | 33.2 | 5.0 |
| M2 | 27.5 | 35.5 | 28.9 | 6.6 |
| M3 | 26.2 | 27.3 | 26.3 | 1.0 |
| M4 | 26.7 | 36.7 | 29.7 | 6.9 |
| M5 | 25.7 | 45.4* | 32.2 | 13.2 |
| no template | 31.0** | 50.8** | 44.4** | |

*Only 1 of 3 replicates with gene-specific target
**$C_T$ values in no template controls indicate non-specific amplification The signals were highly variable among replicates. The low and variable level of specific product may be due to relatively high levels of non-specific amplification (e.g., primer dimer); low $C_T$ values in no template controls provides some evidence for that conclusion. The probe signals were several times higher and less variable in most samples with consensus primers only (FIG. 7B) compared to that using multiple primers. (Note that the fluorescence scale in FIGS. 7B and 7C is twice that used for FIG. 7A.) The exception was target M5, which was amplified in only 1 of 3 replicates containing only the consensus primers, possibly reflecting relatively low amplification efficiency of this target by both limiting and excess primers. The probe signals were only slightly higher in samples that contained the consensus primers plus low concentration of intermediate primers and targets M1, M2, M3, or M4, although SYBR Green $C_T$ values were lowered, indicating improved amplification efficiency of the double stranded product. The failure to obtain much higher probe signals is probably due to the synthesis of sufficient single stranded product after 60 cycles to saturate the probe, used at a concentration of 200 nM. The probe signals in samples with target M5 was high in all 3 replicate samples containing the consensus primers plus intermediate primers, showing the improved amplification due to those additional low-concentration primers.

This example illustrates the power of using thermodynamic consensus primers for detecting one or more homologous targets having considerable sequence variability. This design can be used for both limiting and excess primers in asymmetric PCR, including LATE-PCR and is also likely to have utility in symmetric PCR. Even though initial amplification efficiency may be low, high levels of single stranded product are eventually generated and can be detected using a variety of probing techniques. This example also demonstrates that intermediate primers with homology to limiting primer(s) as well as intermediate primers with homology to excess primer(s) can improve amplification efficiency of the homologs, and can extend the range of variations that can be amplified and detected. In other embodiments, using low concentrations of intermediate primers can also be used with symmetric PCR primers, offering more efficient alternatives to methods such as the use of degenerate primers.

All publications and patents mentioned in the present application are herein incorporated by reference. Various modification and variation of the described methods and compositions will be apparent to those skilled in the art without departing from the scope and spirit of the assays described herein. Although the methods, compositions, and kits have been described in connection with specific exemplary embodiments, it should be understood that the claims should not be unduly limited to such specific embodiments. Indeed, various modifications of the described modes for carrying out the assays described herein that are obvious to those skilled in the relevant fields are intended to be within the scope of the following claims.

We claim:

1. A method for identifying the presence of any of a plurality of related target sequences in a sample, comprising:
   (a) contacting a sample comprising a target sequence that is one of a plurality of related target sequences, wherein said target sequences differ by at least one nucleotide, with a pair of primers for amplifying one or more of said targets, wherein at least one of said primers is a thermodynamic consensus primer that is complementary to at least one of the related target sequences in the sample, and wherein the thermodynamic consensus primer comprises, at the position in which the target sequences differ, a nucleotide that minimizes the differences in melting temperature with the plurality of related target sequences rather than a consensus nucleotide which is the complement of the most common target nucleotide of the different target sequences;
   (b) performing an amplification reaction under conditions such that any of said target sequence, are amplified in a single reaction; and
   (c) detecting an amplification product produced in step (b).

2. The method of claim 1, wherein said plurality of related targets vary at 4 or more nucleotide positions in the region complementary to said at least one thermodynamic consensus primer, wherein the thermodynamic consensus primer comprises, at the positions in which the target sequences differ, nucleotides that minimize the differences in melting temperature with the plurality of related target sequences rather than consensus nucleotides which are the complement of the most common target nucleotides of the different target sequences.

3. The method of claim 1, wherein the concentration of said primers in said pair of primers is at a ratio of at least 5 to 1 and the amplification reaction performed in step (b) is an asymmetric PCR reaction.

4. The method of claim 1, wherein said amplification reaction performed in step (b) is a symmetric PCR reaction.

5. The method of claim 1, wherein one primer of said pair of primers is a limiting primer and one primer of said pair of primers is an excess primer, and wherein the initial melting temperature of said limiting primer with respect to its fully complementary target is higher than or equal to the initial melting temperature of said excess primer with respect its fully complementary target.

6. The method of claim 1, wherein said plurality of related targets are selected from the group consisting of variants of genes, homologs of genes, orthologs of genes, and subtypes of genes.

7. The method of claim 1, wherein said sample comprises two or more of said related target sequences.

8. A method for identifying the presence of any of a plurality of related target sequences in a sample, comprising:
   (a) contacting a sample comprising a target sequence that is one of a plurality of related target sequences that comprises a position that differs in the related target sequences by at least one nucleotide with a first primer and a plurality of second primers for amplifying one of the target sequences, wherein said plurality of second primers are each complementary to a target sequence from among the plurality of related target sequences at the position that differs among the related target sequences by at least one nucleotide, or the complement thereof, and wherein one primer of said plurality of second primers is present at a concentration that is at least 5-fold greater than the concentration of each of the other primers in said plurality of second primers;
   (b) performing an amplification reaction under conditions such that said target sequence is amplified by said first primer and said plurality of second primers in a single reaction; and
   (c) detecting an amplification product produced in step (b).

9. The method of claim 8, wherein said first primer is present at a concentration that is at least 5-fold greater than the concentration of any primer among the plurality of second primers, and wherein the amplification reaction performed in step (b) is an asymmetric PCR reaction.

10. The method of claim 8, wherein said plurality of second primers includes at least one primer that is present at a concentration that is at least 5-fold greater than the concentration of the first primer, and wherein the amplification reaction performed in step (b) is an asymmetric PCR reaction.

11. The method of claim 8, wherein the primer with the highest concentration among said plurality of primers is a thermodynamic consensus primer that comprises, at the position in which the target sequences differ, a nucleotide that minimizes the differences in melting temperature with the plurality of related target sequences rather than a consensus nucleotide which is the complement of the most common target nucleotide of the different target sequences.

12. The method of claim 9, wherein the initial melting temperature of each of said plurality of second primers with respect to its fully complementary target is higher than or equal to the initial melting temperature of said first primer with respect its fully complementary target.

13. The method of claim 8, wherein said plurality of related targets are selected from the group consisting of variants of genes, homologs of genes, orthologs of genes, and subtypes of genes.

14. The method of claim 13, wherein said genes are from an organism selected from the group consisting of pathogenic agents, animals, and other organisms of interest.

15. The method of claim 14, wherein said genes are from a pathogenic agent selected from the group consisting of viruses, bacteria, and fungi.

16. The method of claim 14, wherein said genes are from an animal selected from the group consisting of humans, livestock, and companion animals.

17. The method of claim 8, wherein said sample comprises two or more of said related target sequences.

* * * * *

SEQUENCE LISTING

<160> NUMBER OF SEQ ID NOS: 13

<210> SEQ ID NO 1
<211> LENGTH: 105
<212> TYPE: DNA
<213> ORGANISM: Artificial Sequence
<220> FEATURE:
<223> OTHER INFORMATION: Synthetic

<400> SEQUENCE: 1
agaagaaggg cccagggttg gactctgagt ggtgtcaaga gctagcaaag gcctggggca     60
gtatgtctcc gcgcgtttca tgcggatcaa aagctcagtg atggt                    105

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
agggcccagg gttggactc                                                  19

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
atagctcttg acaccactca t                                               21

<210> SEQ ID NO 4
<211> LENGTH: 32
<212> TYPE: DNA
<213> ORGANISM: Artificial Sequence
<220> FEATURE:
<223> OTHER INFORMATION: Synthetic

<400> SEQUENCE: 4
accatcactg agctgttgat tcgcatgaag cg                                   32

<210> SEQ ID NO 5
<211> LENGTH: 32
<212> TYPE: DNA
<213> ORGANISM: Artificial Sequence
<220> FEATURE:
<223> OTHER INFORMATION: Synthetic

<400> SEQUENCE: 5
accatcactg agcttttgat ccgcatgaag cg                                   32

<210> SEQ ID NO 6
<211> LENGTH: 32
<212> TYPE: DNA
<213> ORGANISM: Artificial Sequence
<220> FEATURE:
<223> OTHER INFORMATION: Synthetic

<400> SEQUENCE: 6
accatcactg agctgttgat ccgcatgaaa cg                                   32

<210> SEQ ID NO 7
<211> LENGTH: 32

```
<212> TYPE: DNA
<213> ORGANISM: Artificial Sequence
<220> FEATURE:
<223> OTHER INFORMATION: Synthetic

<400> SEQUENCE: 7
accatcacgg agctgttgat ccgcatgaag cg                               32

<210> SEQ ID NO 8
<211> LENGTH: 35
<212> TYPE: DNA
<213> ORGANISM: Artificial Sequence
<220> FEATURE:
<223> OTHER INFORMATION: Synthetic

<400> SEQUENCE: 8
gacaccatca ctgagctttt gattcgcatg aaacg                            35

<210> SEQ ID NO 9
<211> LENGTH: 32
<212> TYPE: DNA
<213> ORGANISM: Artificial Sequence
<220> FEATURE:
<223> OTHER INFORMATION: Synthetic

<400> SEQUENCE: 9
accatcactg agctcttgat ccgcatgaaa cg                               32

<210> SEQ ID NO 10
<211> LENGTH: 34
<212> TYPE: DNA
<213> ORGANISM: Artificial Sequence
<220> FEATURE:
<223> OTHER INFORMATION: Synthetic

<400> SEQUENCE: 10
ggaccatcac tgagcttttg atccgcatga aacg                             34

<210> SEQ ID NO 11
<211> LENGTH: 32
<212> TYPE: DNA
<213> ORGANISM: Artificial Sequence
<220> FEATURE:
<223> OTHER INFORMATION: Synthetic

<400> SEQUENCE: 11
aacatcactg agctcctgat ccgcatgaaa cg                               32

<210> SEQ ID NO 12
<211> LENGTH: 35
<212> TYPE: DNA
<213> ORGANISM: Artificial Sequence
<220> FEATURE:
<223> OTHER INFORMATION: Synthetic

<400> SEQUENCE: 12
ggcaccatta ctgagctttt gatccgcatg aaacg                            35

<210> SEQ ID NO 13
<211> LENGTH: 32
<212> TYPE: DNA
```

```
<213> ORGANISM: Artificial Sequence
<220> FEATURE:
<223> OTHER INFORMATION: Synthetic

<400> SEQUENCE: 13
agcatcacgg agttgttgat ccgcatcaaa cg                                    32
```